United States Patent
Powell et al.

(10) Patent No.: US 10,034,924 B2
(45) Date of Patent: Jul. 31, 2018

(54) METHODS AND COMPOSITIONS FOR ENHANCED CELLULAR SELECTIVITY USING NANOCARRIER-ASSOCIATED LIGANDS

(71) Applicant: THE JOHNS HOPKINS UNIVERSITY, Baltimore, MD (US)

(72) Inventors: Jonathan Powell, Baltimore, MD (US); Ying-Chun Lo, Baltimore, MD (US); Michael Edidin, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/106,400

(22) PCT Filed: Dec. 22, 2014

(86) PCT No.: PCT/US2014/071890
§ 371 (c)(1),
(2) Date: Jun. 20, 2016

(87) PCT Pub. No.: WO2015/095866
PCT Pub. Date: Jun. 25, 2015

(65) Prior Publication Data
US 2016/0339091 A1 Nov. 24, 2016

Related U.S. Application Data

(60) Provisional application No. 61/919,209, filed on Dec. 20, 2013.

(51) Int. Cl.
| | |
|---|---|
| *C12N 5/0783* | (2010.01) |
| *A61K 39/00* | (2006.01) |
| *A61K 47/69* | (2017.01) |
| *A61K 47/68* | (2017.01) |
| *A61K 39/39* | (2006.01) |
| *A61K 47/48* | (2006.01) |

(52) U.S. Cl.
CPC .......... *A61K 39/0011* (2013.01); *A61K 39/39* (2013.01); *A61K 47/48561* (2013.01); *A61K 47/48884* (2013.01); *A61K 47/6849* (2017.08); *A61K 47/6929* (2017.08); *C12N 5/0636* (2013.01); *C12N 5/0638* (2013.01); *A61K 2039/55516* (2013.01); *C12N 2501/515* (2013.01); *C12N 2501/599* (2013.01); *C12N 2531/00* (2013.01)

(58) Field of Classification Search
CPC .......... A61K 39/0011; A61K 47/48884; A61K 47/48561; A61K 39/39; A61K 2039/55516; C12N 5/0638; C12N 5/0636; C12N 2501/515; C12N 2531/00
See application file for complete search history.

(56) References Cited

PUBLICATIONS

International Search Report and Written Opinion dated Mar. 31, 2015, from related PCT Patent Application No. PCT/US14/071890.
Lo, Ying-Chun et al., "Selective activation of antigen-experienced T cells by anti-CD3 constrained on nanoparticles," The Journal of Immumology, Epubl Oct. 4, 2013, vol. 191, No. 10, pp. 5107-5114.
Kumar, Rashmi et al., "Increased sensitivity of antigen-experienced T cells through the enrichment of oligomeric T cell receptor complexes," Immunity, 2011, vol. 35, No. 3, pp. 375-387.
Pastor, Silvia et al., "Analyses of TCR clustering at the T cell-antigen-presenting cell interface and its impact on the activation of naive CD4+ T cells," International Immunology, 2007, vol. 18, No. 11, pp. 1615-1625.
Molnar, Eszter et al., "Pre-clustered TCR complexes," FEBS letters, 2010, vol. 584, No. 24, pp. 4832-4837.
Blattman, Joseph N. et al., "Cancer immunotherapy: a treatment for the masses," Science, 2004, vol. 305, No. 5681, pp. 200-205.
Perica, Karlo et al., "Linking form to function: Biophysical aspects of artificial antigen presenting cell design," Biochimica et Biophysica Acta (BBA)-Molecular Cell Research, Epub. Sep. 6, 2014, vol. 1853, Issue 4, pp. 781-790.

*Primary Examiner* — Daniel C Gamett
(74) *Attorney, Agent, or Firm* — Casimir Jones, S.C.; Jeffrey W. Childers

(57) ABSTRACT

The presently disclosed subject matter provides methods and compositions for activation of clustered receptors on a target cell using nanocarrier-associated ligands, particularly methods and compositions for targeted activation of clustered receptors on antigen-experienced T cells using nanocarrier-associated antibodies.

38 Claims, 28 Drawing Sheets

METHODS AND COMPOSITIONS FOR ENHANCED CELLULAR SELECTIVITY USING NANOCARRIER-ASSOCIATED LIGANDS

CROSS-REFERENCE TO RELATED APPLICATIONS

This application is a 35 U.S.C. § 371 National Stage Entry of International Application No. PCT/US14/071890 having an international filing date of Dec. 22, 2014, which claims the benefit of U.S. Provisional Application No. 61/919,209, filed Dec. 20, 2013, each of which is incorporated herein by reference in their entirety.

FEDERALLY SPONSORED RESEARCH OR DEVELOPMENT

This invention was made with United States government support under P01AI072677 and R561AI099276 awarded by the National Institutes of Health (NIH). The U.S. government has certain rights in the invention.

BACKGROUND

Specificity and memory are key features of the adaptive immune system (Bonilla et al. (2010) *J. Allergy Clin. Immunol.* 125:S33-S40; Litman et al. (2010) *Nat. Rev. Immunol.* 10:543-553). An adaptive immune response amplifies a small population of antigen (Ag) specific B and T lymphocytes to promote the clearance of an infection. Although B cell receptors (antibodies) can recognize soluble intact Ag, T cells recognize cognate peptides presented in the context of major histocompatibility complex (MHC) molecules on the surface of antigen presenting cells (APCs) (Davis et al. (1988) *Nature* 334:395-402).

Antibodies have exquisite specificity for their antigen. Thus, antibodies have great therapeutic potential in terms of selectively targeting receptors to either promote or inhibit receptor activity. Likewise, antibodies can target infected or tumor cells by recognizing their antigen on the cell of interest. However, the exquisite specificity imparted by the antibody-antigen interaction can be abrogated by the expression of the target receptor on "off target" cells. For example, soluble anti-CD3 will activate all T cells, not just the T cells of interest. Likewise, anti-CTLA-4 and anti-PD-1 will block these molecules on all T cells, not just the T cells of interest. In fact, a major hurdle for anti-CD3 agonistic and anti-PD-1 (and anti-CTLA-4) antibodies is that they cause non-specific T cell activation and at times life threatening autoimmunity.

The concept of the dichotomy of selective target specificity in the absence of cellular specificity can also be extended generically to receptor-ligand interactions. In other words, the administration of a ligand might have great specificity for a receptor, but if the receptor is found both on cells of interest and "normal" cells, this specificity is in part negated (Lim and Levy (2014) *J. Immunol.* 193(4):1519-24).

A fundamental tenet of immunotherapy for cancer is the ability of effectors of the immune system to specifically target cancer cells, while leaving normal cells unscathed. In spite of tremendous advances in understanding antigen specificity and developing vaccines, until very recently immunotherapy for cancer has not lived up to its potential. This is because tumors develop means to evade the endogenous immune destruction by usurping negative regulatory pathways inherent to the immune response. Blocking these pathways with anti-CTLA-4 and anti-PD-1 antibodies, so called checkpoint blockade, has led to meaningful clinical responses in patients. The utility of this strategy is limited, in part, however, by the fact that checkpoint blockade non-selectively enhances T cell responses thus leading to autoimmunity. A strategy that promotes checkpoint blockade for anti-tumor responses without non-selectively activating the immune system is desirable.

SUMMARY

The presently disclosed subject matter provides methods and compositions for activation of microclustered receptors on a target cell using nanocarrier-associated ligands.

In one aspect, the presently disclosed subject matter is directed to a method for selectively enhancing activation of antigen-experienced cells, the method comprising: a) administering a selected antigen to target cells in an amount sufficient to produce microclustering of ligand-binding receptors on the surface of the target cells, thereby producing antigen-experienced cells comprising microclustered ligand-binding receptors; and b) administering nanocarrier-associated ligands and the selected antigen to a plurality of cells, wherein the plurality of cells comprises antigen-experienced cells and naïve cells; wherein the nanocarrier-associated ligands bind microclustered ligand-binding receptors of the antigen-experienced cells, thereby selectively enhancing activation of the antigen-experienced cells as compared to: i) the binding of free ligands to the microclustered ligand-binding receptors; and/or ii) the binding of nanocarrier-associated ligands to ligand-binding receptors of naïve cells, wherein the naïve cells are non-specifically activated. In some aspects, the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials. In other aspects, the nanocarrier-associated ligands are associated with nanocarriers with a mean geometric diameter that is less than 100 nm.

In another aspect, the presently disclosed subject matter is directed to a method for treating infectious disease or cancer in a subject in need thereof, the method comprising administering to the subject: a) a selected antigen in an amount sufficient to produce microclustering of ligand-binding receptors on the surface of target cells in the subject, thereby producing antigen-experienced cells comprising microclustered ligand-binding receptors; and b) nanocarrier-associated ligands in an amount sufficient for the nanocarrier-associated ligands to bind microclustered ligand-binding receptors of the antigen-experienced cells, thereby selectively enhancing activation of the antigen-experienced cells as compared to: i) the binding of free ligands to the microclustered ligand-binding receptors; and/or ii) the binding of nanocarrier-associated ligands to ligand-binding receptors of naïve cells, wherein the naïve cells are non-specifically activated. In some aspects, the selected antigen and the nanocarrier-associated ligands are administered to the subject concurrently. In other aspects, the selected antigen and the nanocarrier-associated ligands are administered to the subject sequentially.

In some aspects of the presently disclosed methods, the antigen-experienced cells and the naïve cells are both T cells, particularly wherein the T cells are selected from the group consisting of $CD4^+$ T cells or $CD8^+$ T cells. In other aspects, selectively enhancing activation of the antigen-experienced cells comprises selectively enhancing an antigen-specific T cell response in the antigen-experienced cells as compared to the naïve cells. In other aspects, the antigen-specific T cell response comprises enhanced proliferation of the antigen-experienced cells as compared to the naïve cells. In further aspects, the antigen-specific T cell response comprises promoting the generation and function of specific effector cells from the antigen-experienced cells as compared to the naïve cells. In still further aspects, promoting the generation and function of specific effector cells from the antigen-experienced cells comprises increasing the number of antigen-experienced cells producing one or more proteins, particularly wherein the one or more proteins comprise interleukins, and more particularly wherein the interleukins comprise IL-12 or IL-4. In still further aspects, the antigen-specific T cell response comprises enhancing the response of the antigen-experienced cells to a vaccine as compared to the naïve cells, particularly vaccine-induced proliferation of antigen-experienced cells and generation of functional memory cells. In other aspects, the antigen is a protein or peptide. In some aspects, the ligand-binding receptors are T cell receptors, particularly wherein the ligands are selected from the group consisting of anti-CD3 antibodies, anti-PD-1 antibodies, and functional variants thereof. In some aspects, the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials. In other aspects, the nanocarrier-associated ligands are associated with nanocarriers with a mean geometric diameter that is less than 100 nm.

In further aspects, the presently disclosed subject matter is directed to a method for selectively enhancing activation of cells comprising microclustered ligand-binding receptors, the method comprising administering nanocarrier-associated ligands to a plurality of cells, wherein the plurality of cells comprises: a) cells comprising microclustered ligand-binding receptors; and b) cells comprising non-microclustered ligand-binding receptors; wherein the nanocarrier-associated ligands selectively bind microclustered ligand-binding receptors, thereby selectively enhancing activation of cells comprising microclustered ligand-binding receptors as compared to cells comprising non-microclustered ligand-binding receptors. In some aspects, the cells comprising microclustered ligand-binding receptors comprise cancer cells, particularly wherein the nanocarrier-associated ligands are anti-cancer agents, and wherein selectively enhancing activation of cells comprising microclustered ligand-binding receptors comprises destroying the cancer cells.

In other aspects, the presently disclosed subject matter is directed to a composition for selectively enhancing activation of antigen-experienced cells, the composition comprising: a) a selected antigen in an amount sufficient to produce microclustering of ligand-binding receptors on the surface of target cells, thereby producing antigen-experienced cells comprising microclustered ligand-binding receptors; and b) nanocarrier-associated ligands in an amount sufficient for the nanocarrier-associated ligands to bind microclustered ligand-binding receptors of the antigen-experienced cells, thereby selectively enhancing activation of the antigen-experienced cells as compared to: i) the binding of free ligands to the microclustered ligand-binding receptors; and/or ii) the binding of nanocarrier-associated ligands to ligand-binding receptors of naïve cells, wherein the naïve cells are non-specifically activated. In some aspects, the antigen-experienced cells and the naïve cells are both T cells, particularly wherein the T cells are selected from the group consisting of $CD4^+$ T cells or $CD8^+$ T cells. In other aspects, the antigen is a protein or peptide. In some aspects, the ligand-binding receptors are T cell receptors, particularly wherein the ligands are selected from the group consisting of anti-CD3 antibodies, anti-PD-1 antibodies, and functional variants thereof. In some aspects, the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials. In other aspects, the nanocarrier-associated ligands are associated with nanocarriers with a mean geometric diameter that is less than 100 nm.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
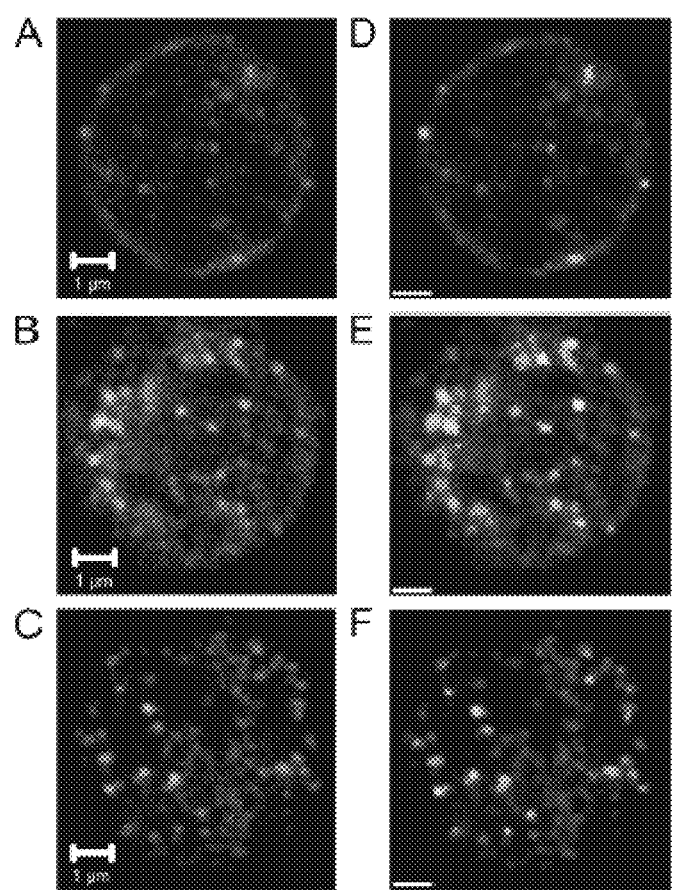
Figure 1:
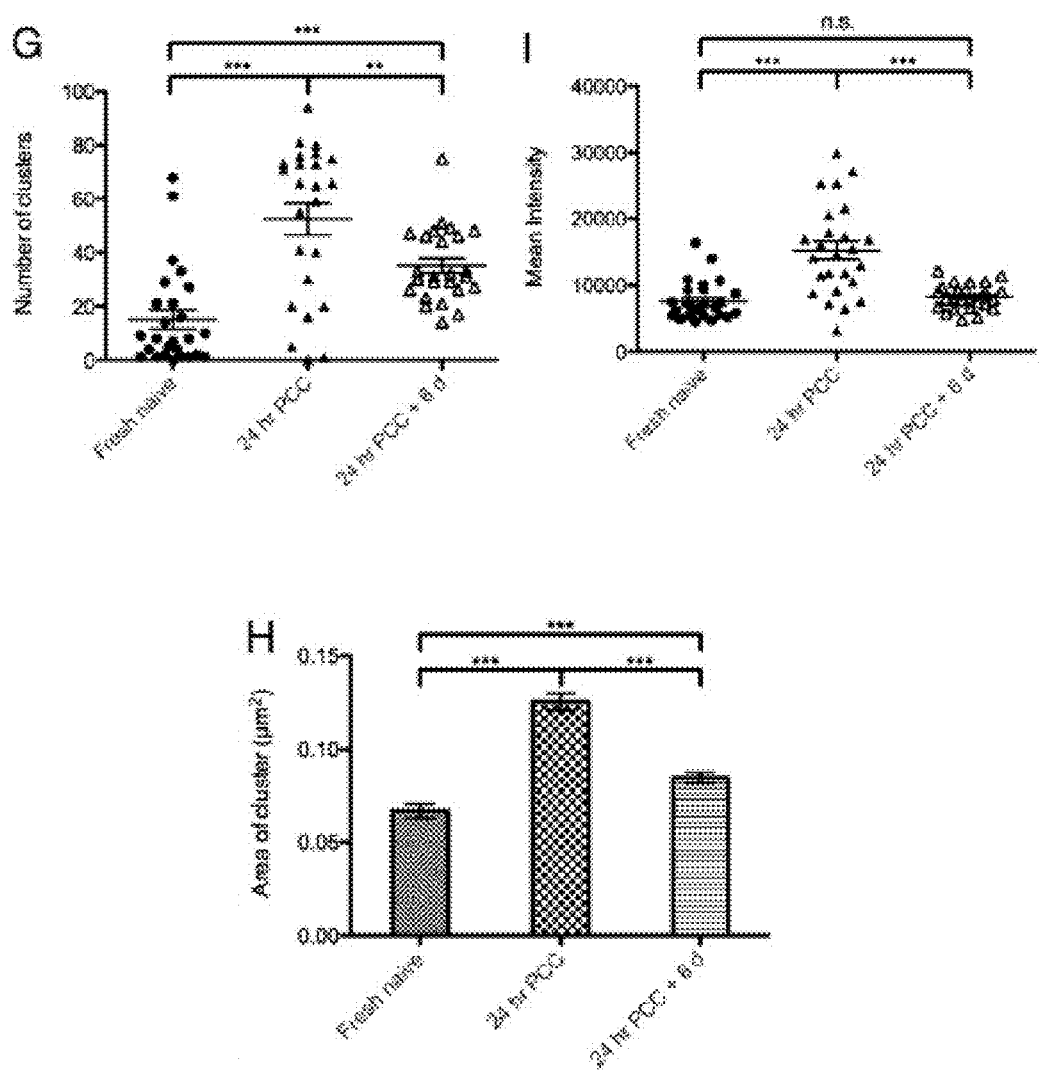
Figure 2:
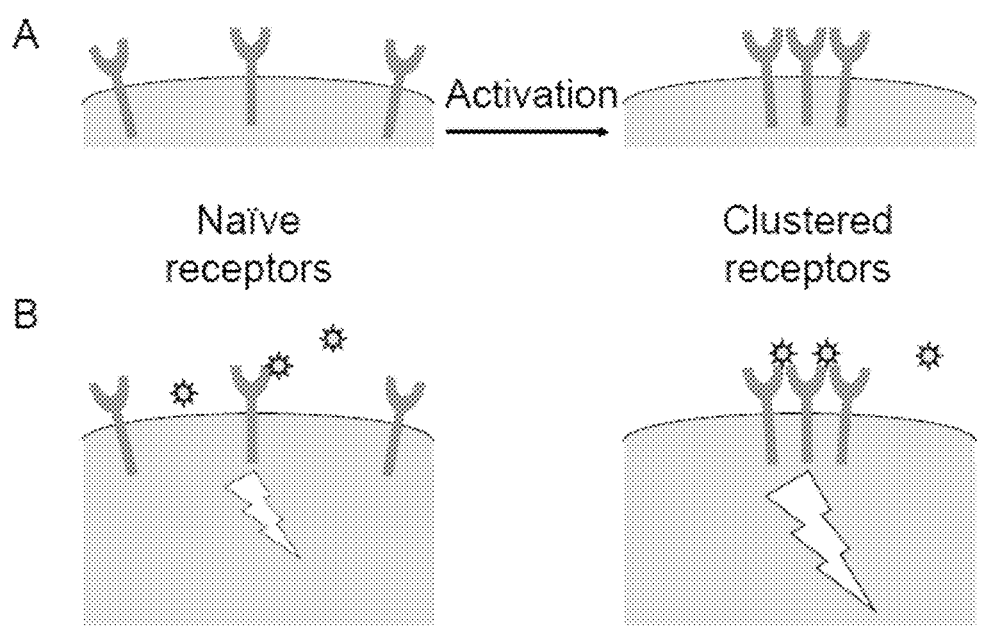
Figure 3:
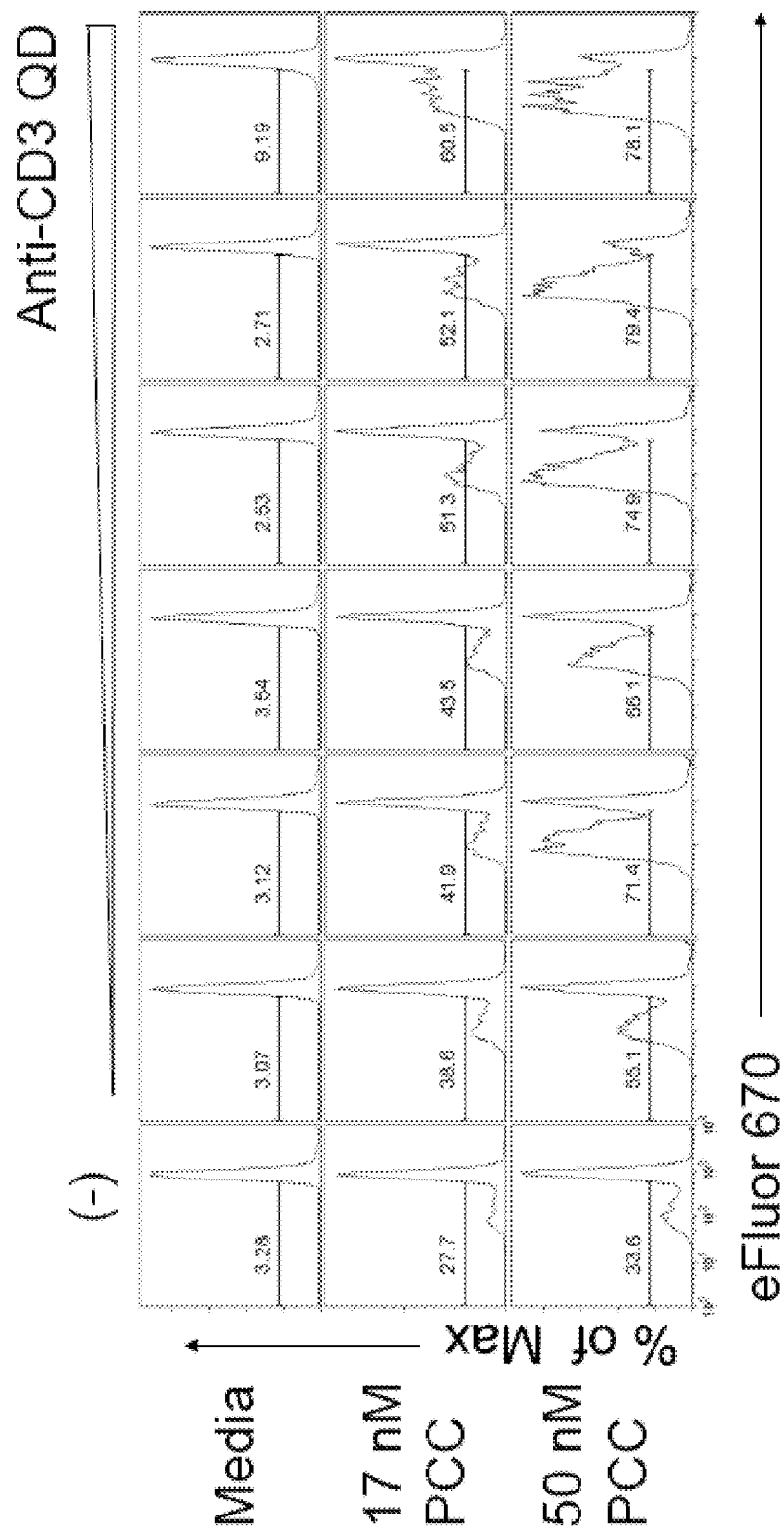
Figure 4:
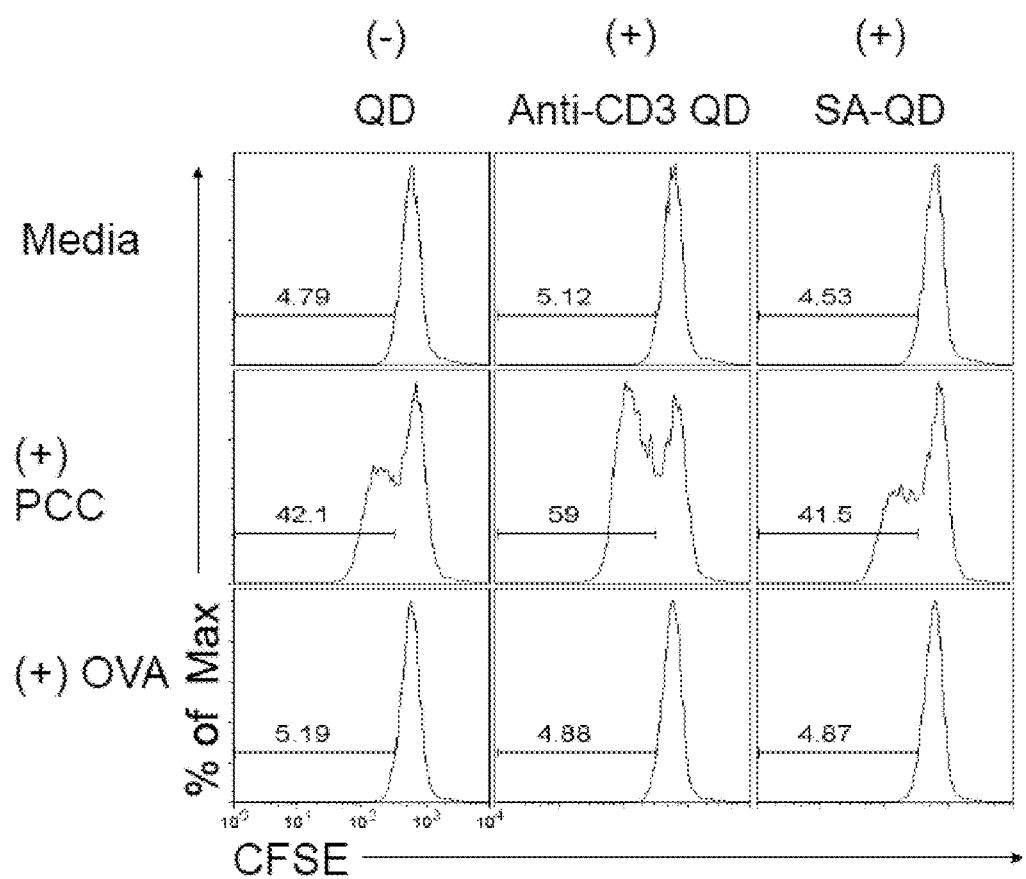
Figure 5:
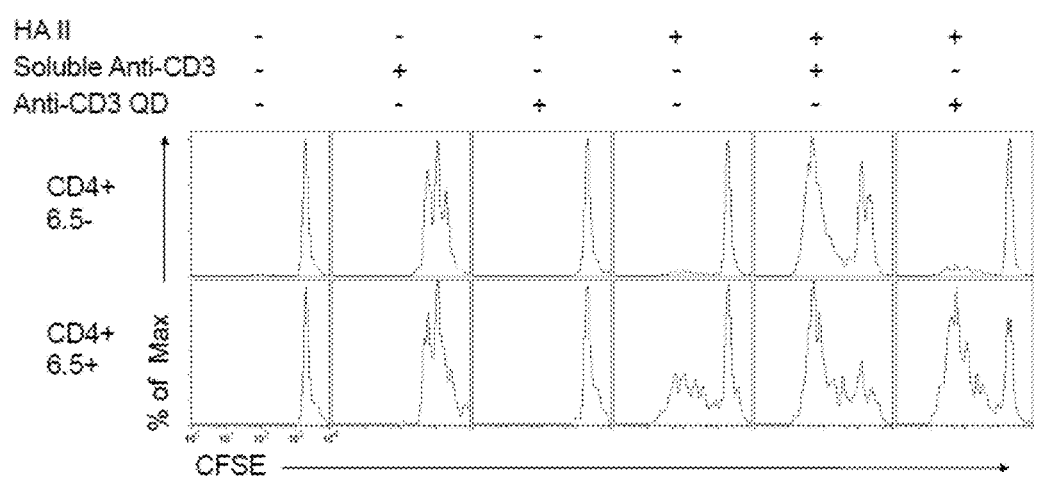
Figure 6:
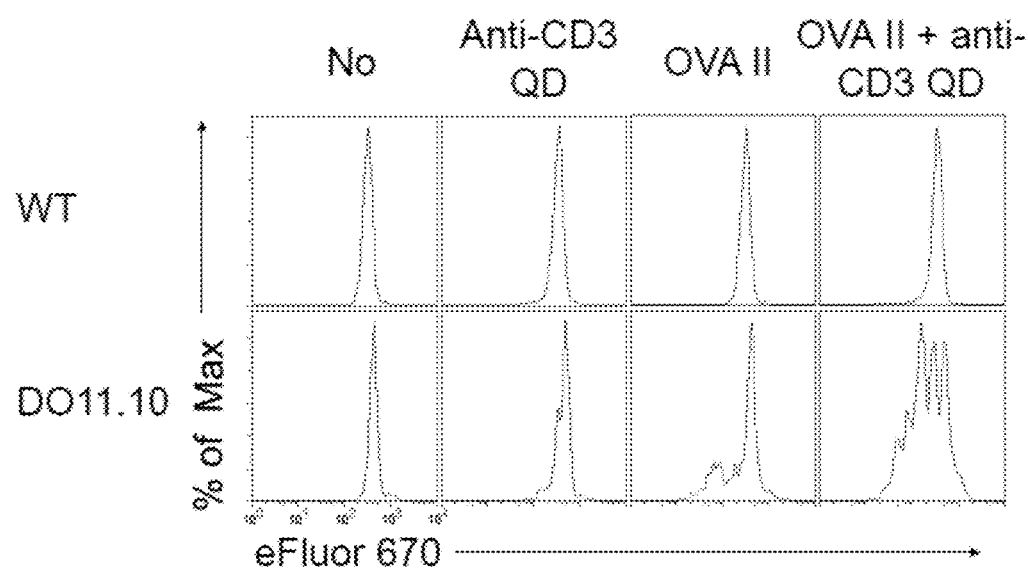
Figure 7:
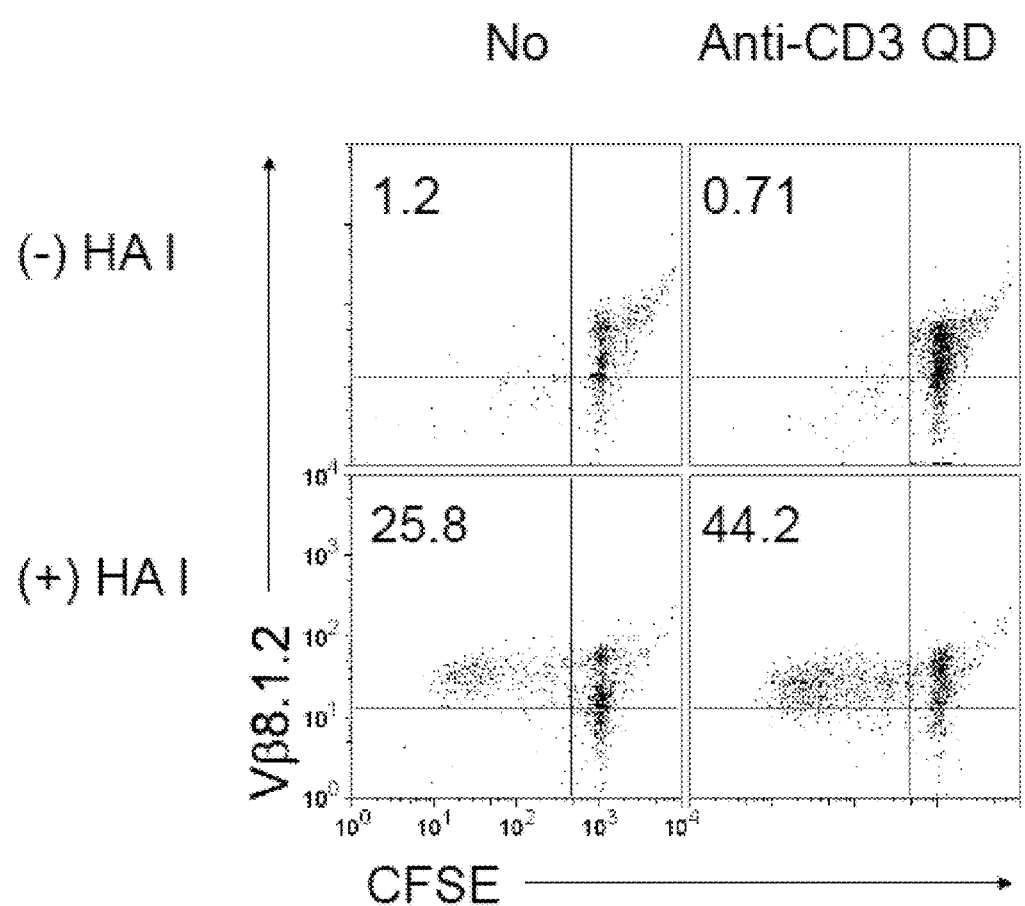
Figure 8:
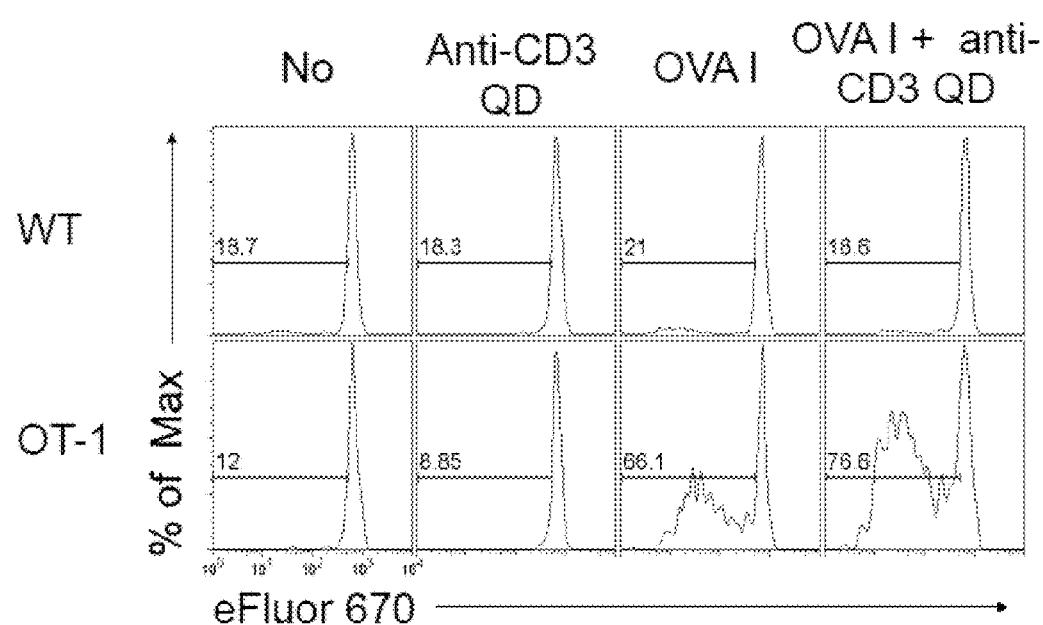
Figure 9:
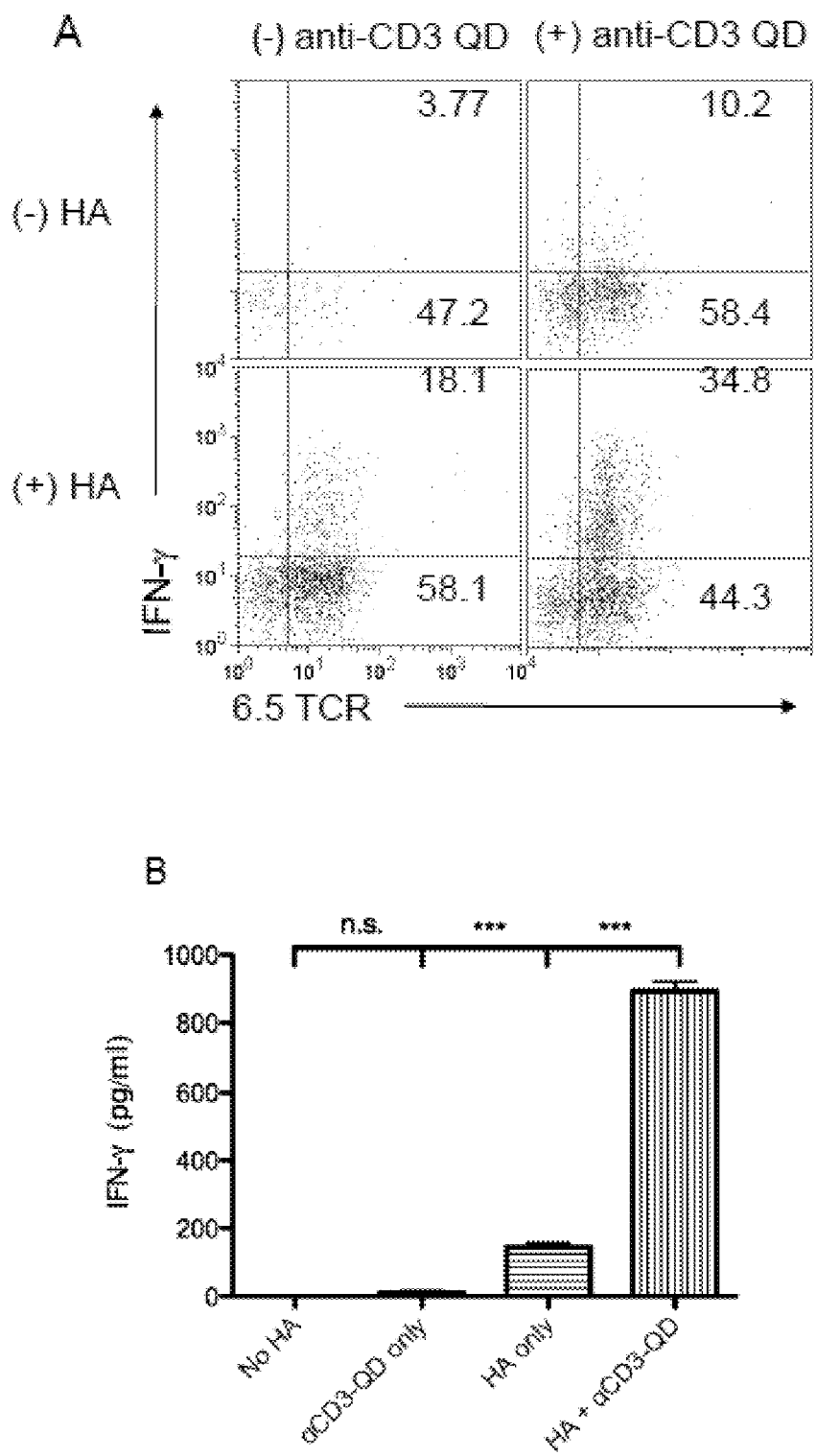
Figure 10:
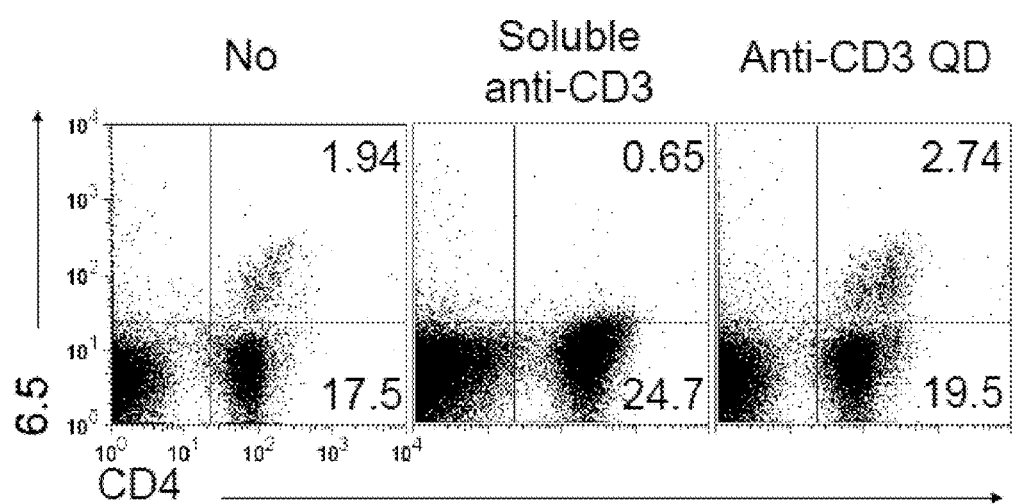
Figure 11:
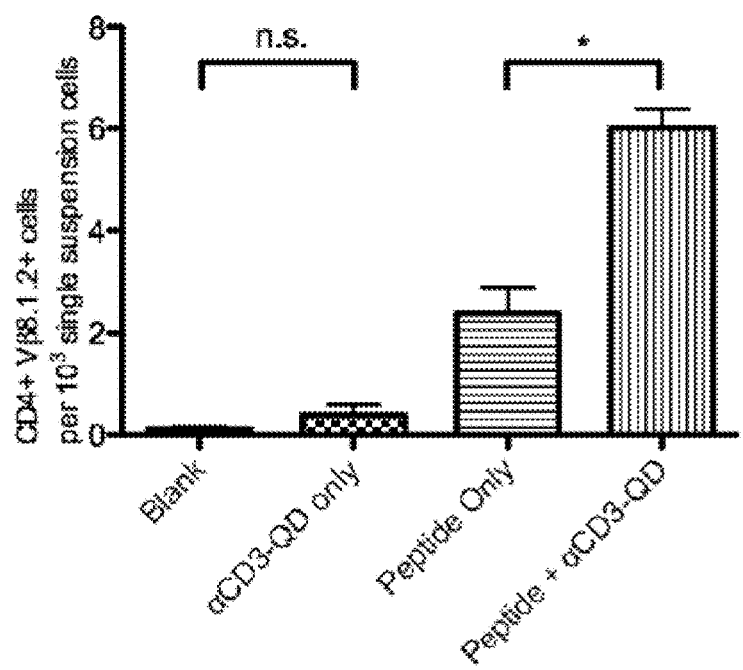
Figure 12:
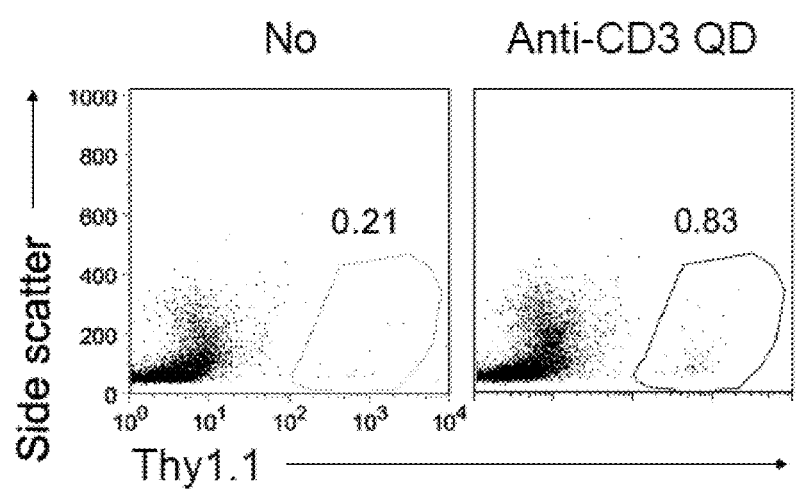
Figure 13:
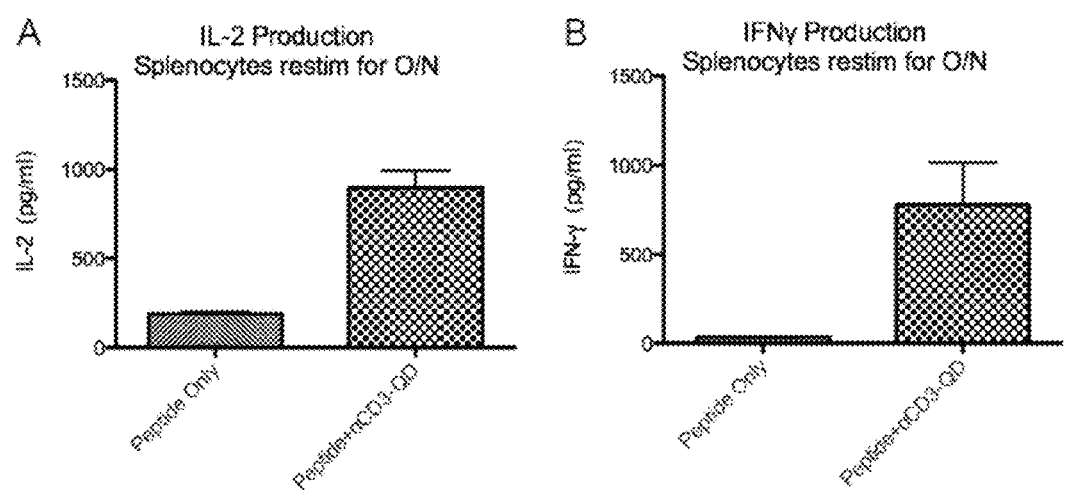
Figure 14:
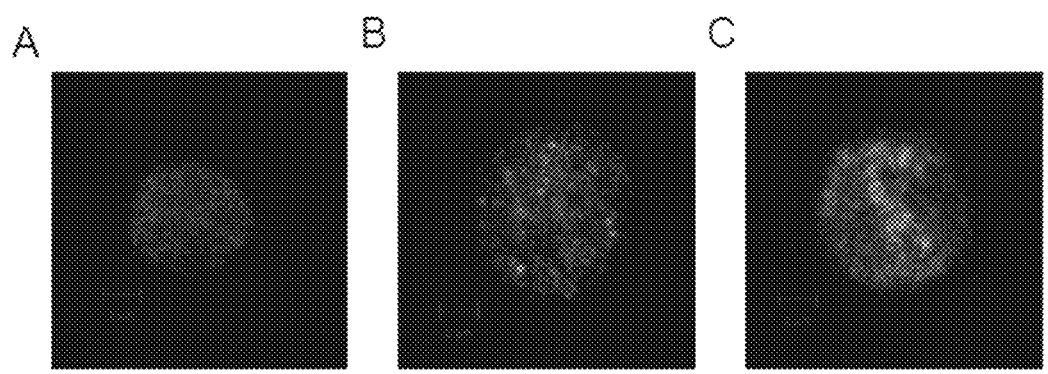
Figure 15:
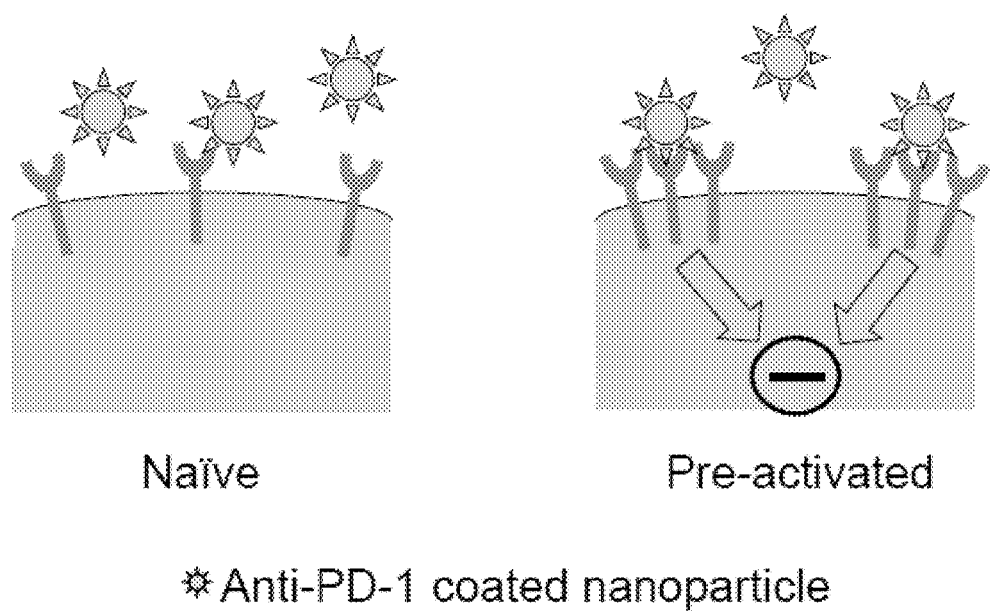
Figure 16:
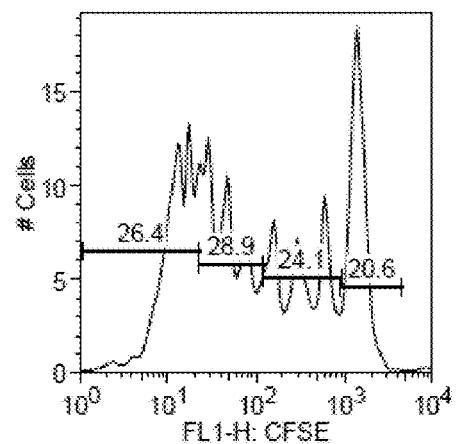
Figure 16:
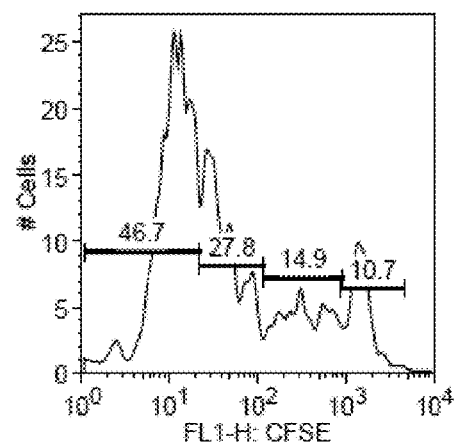
Figure 16:
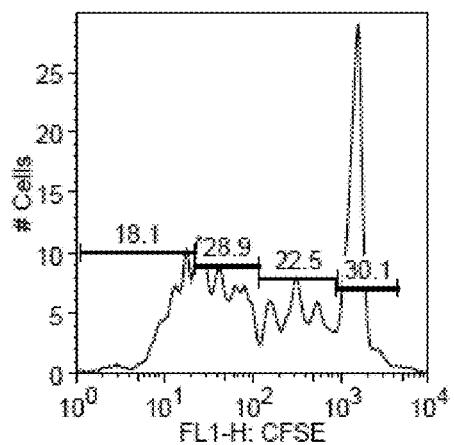
Figure 17:
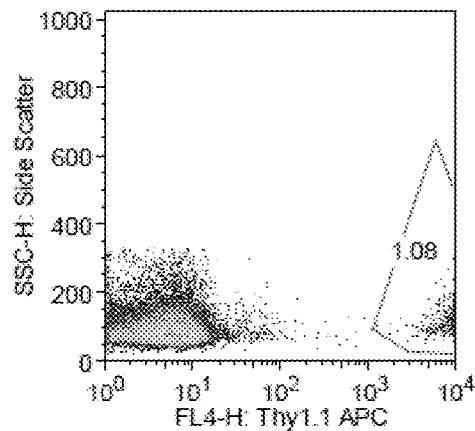
Figure 17:
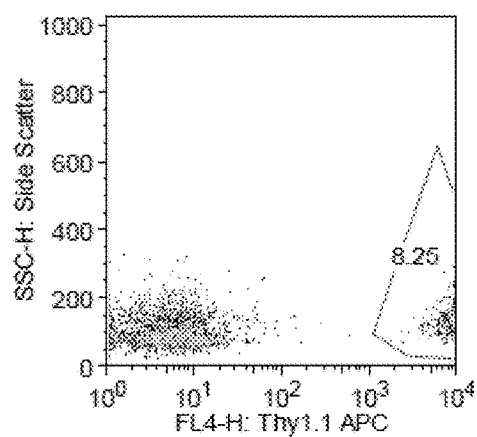
Figure 17:
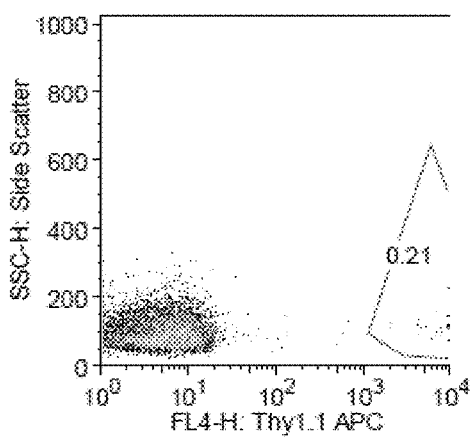
Figure 18A:
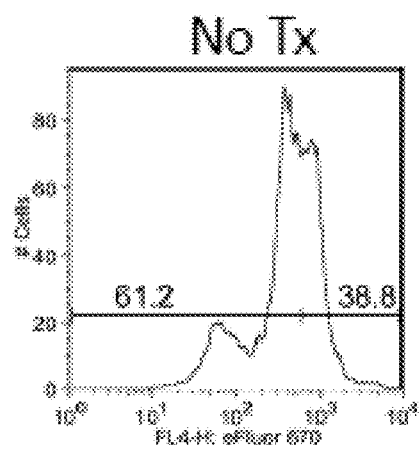
Figure 18A:
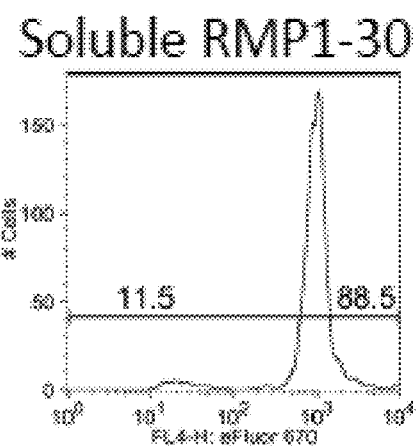
Figure 18A:
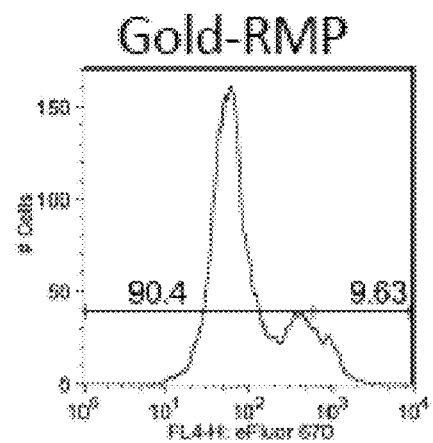
Figure 18B:
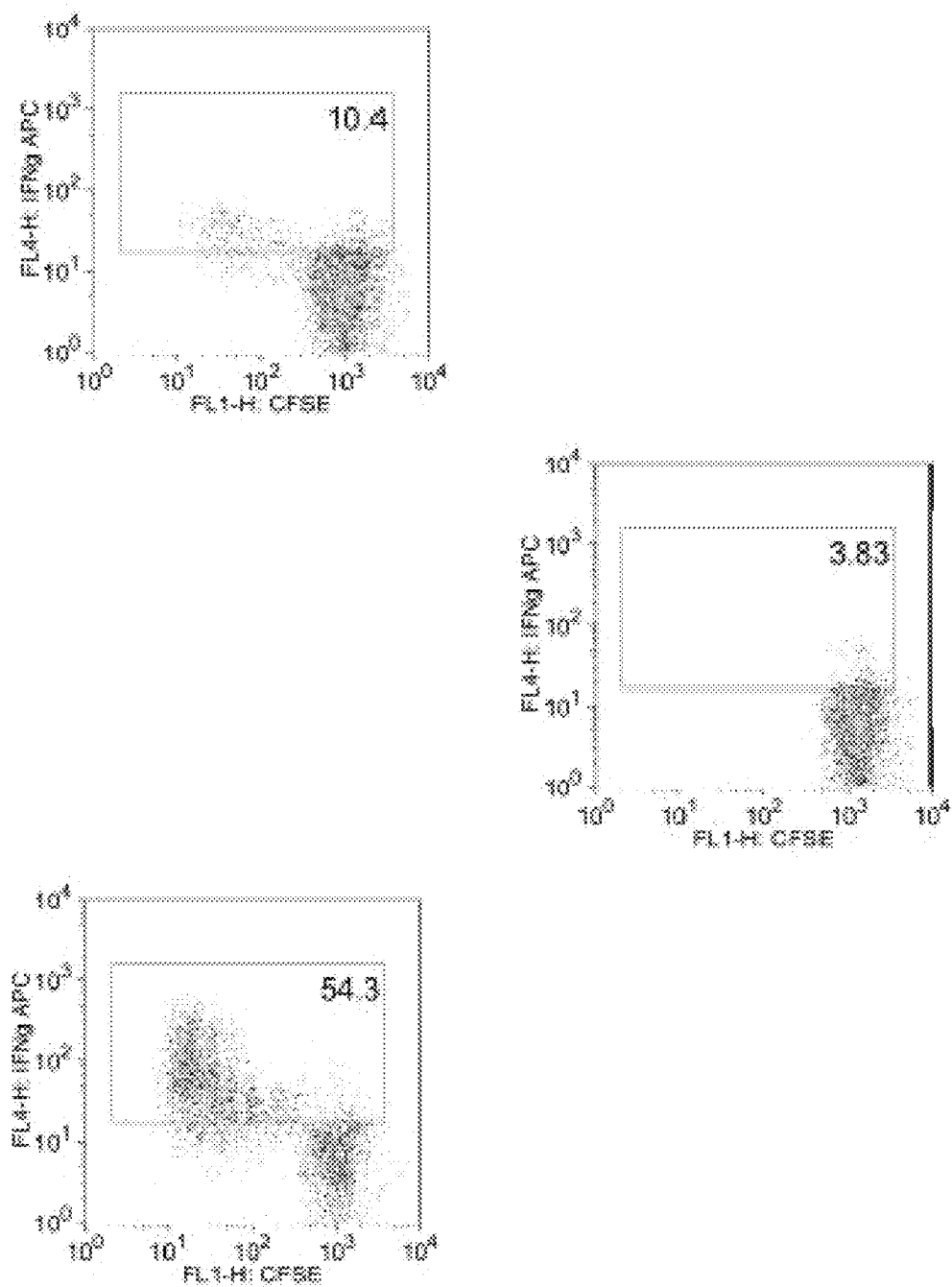
Figure 18C:
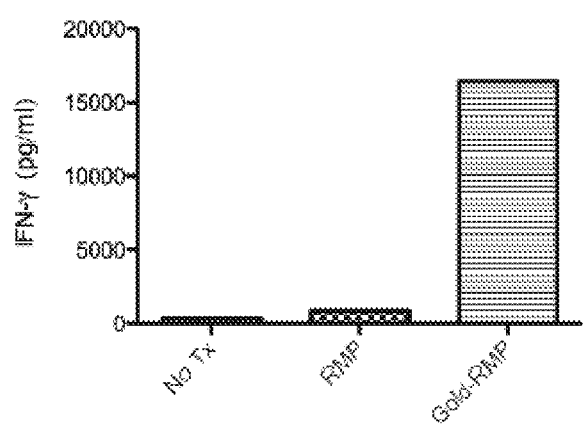
Figure 19:
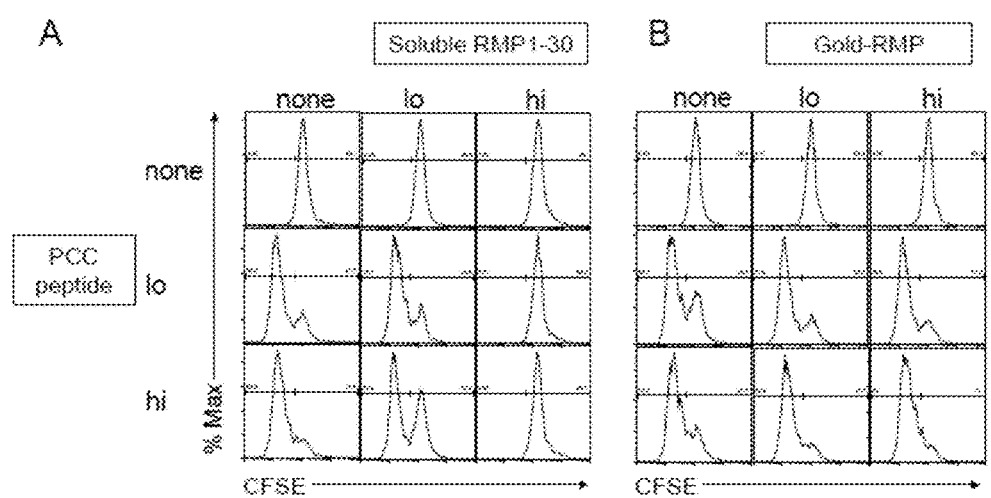
Figure 20:
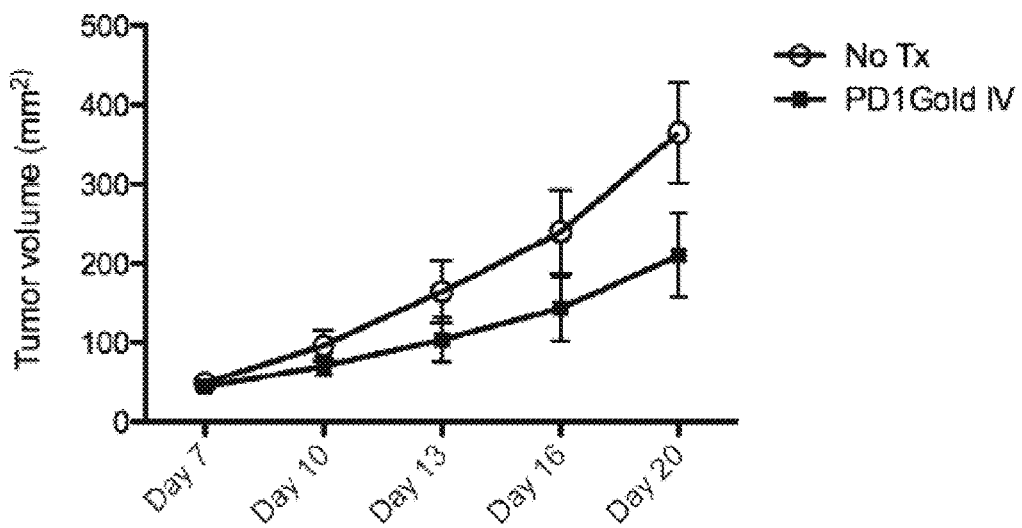
Figure 21:
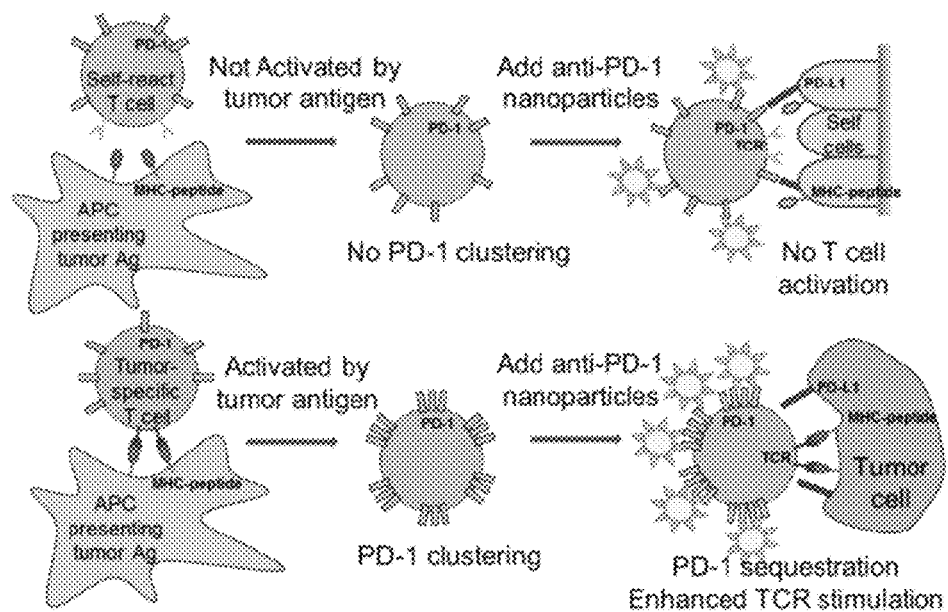
Figure 23:
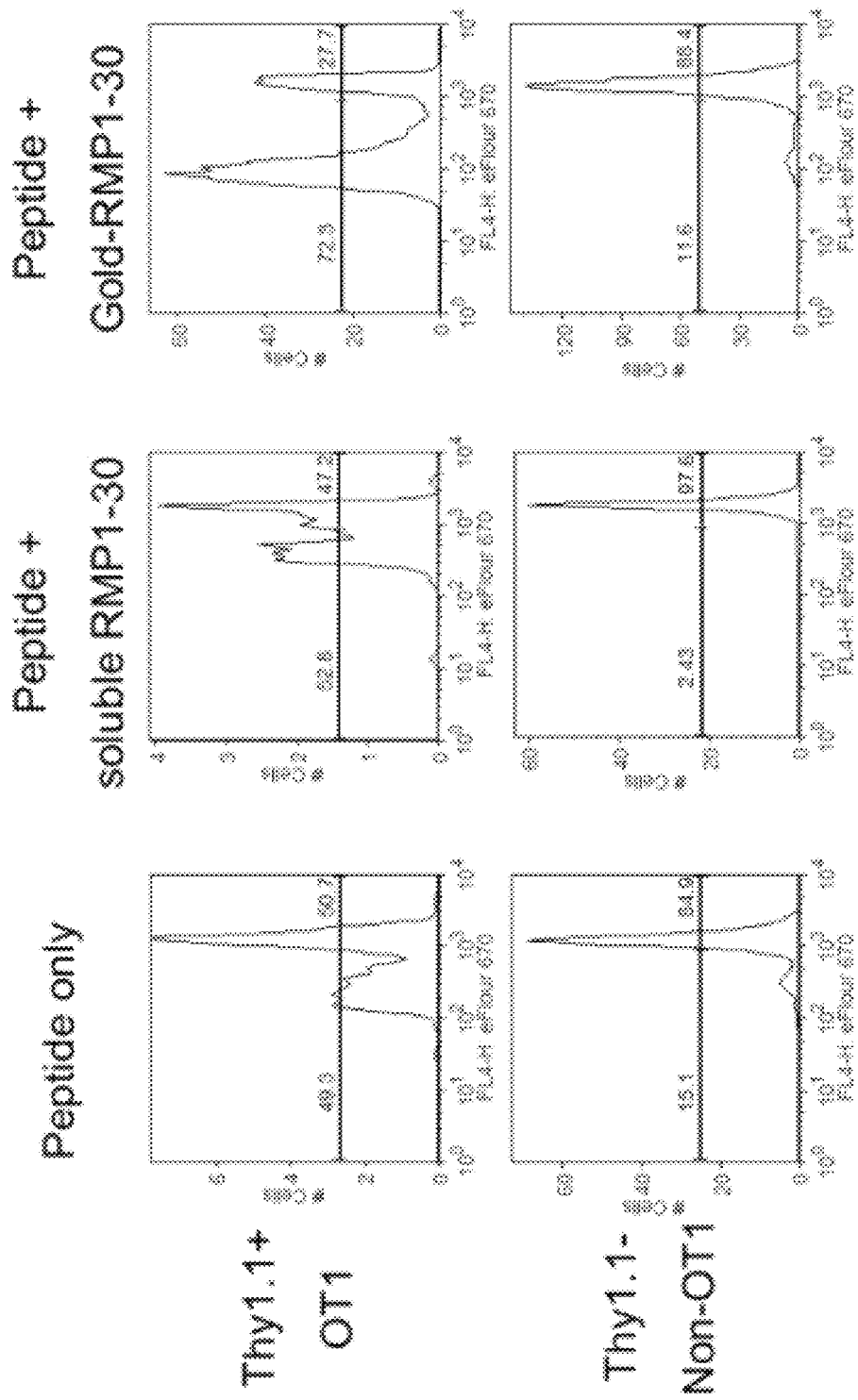
Figure 24:
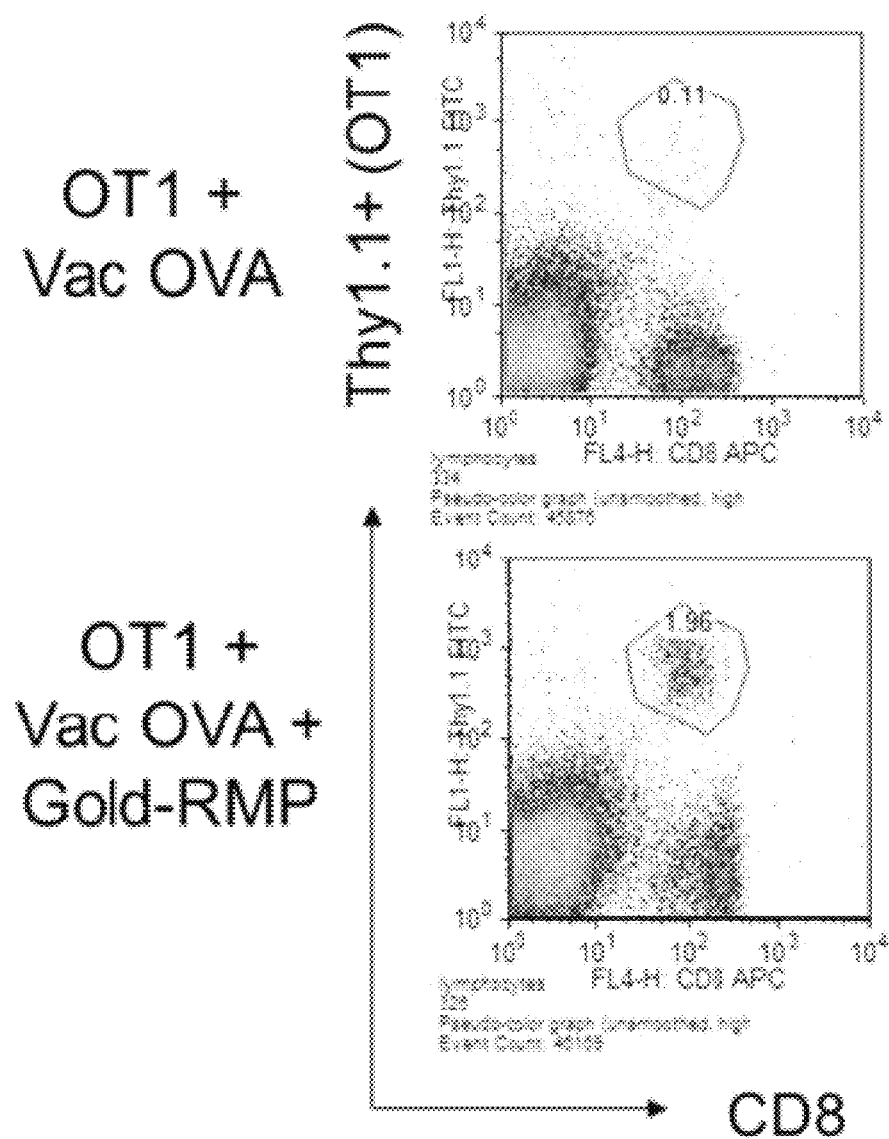
Figure 25:
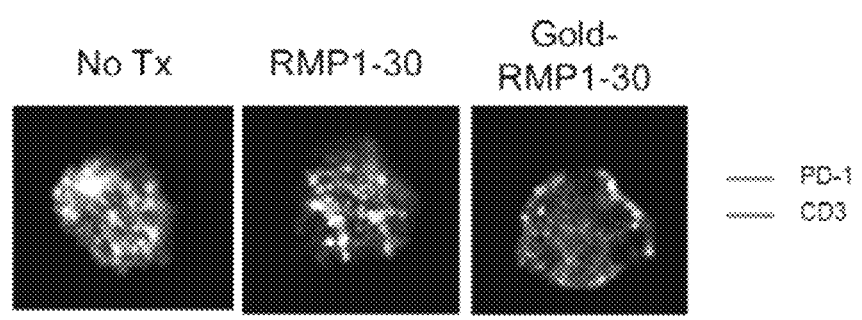

Having thus described the presently disclosed subject matter in general terms, reference will now be made to the accompanying Figures, which are not necessarily drawn to scale, and wherein:

FIGS. 1A-1I show antigen (Ag) stimulation induces T cell receptor (TCR) clustering. Fresh naïve 5C.C7 splenocytes (A) and 5C.C7 splenocytes stimulated with 50 nM pigeon cytochrome C (PCC) for 24 h (B) were fixed by 2% formaldehyde, stained for CD3, and imaged by confocal microscopy. (D-F) Microclusters were classified by size and size classes color-coded using Volocity imaging analysis software. Objects with area <0.01 $\mu m^2$ were excluded. Scale bars, 1 µm. (G) The average number of microclusters identified on each cell (n≥25). (H) The average area of each microcluster. (I) The mean intensity of each cell (n≥25). Data are representative of three independent experiments. $p>0.01$, *$p<0.001$ (two-tailed t test);

FIGS. 2A and 2B show a schematic representation of how anti-CD3 quantum dots (QD) activate Ag-experienced cells. (A) Receptors are mostly dispersed on the surface of a naïve T cell. Upon activation, receptors cluster. (B) The dispersed receptors are not readily cross linked by binding of a ligand-coated nanoparticle, and this interaction delivers a minimal signal. However, ligand-coated nanoparticles can bind multiple receptors in a cluster; this induces strong signaling;

FIG. 3 shows eFluor 670 dilution in naïve 5C.C7 splenocytes stimulated for 3 d with 0, 17, or 50 nM PCC in combination with various concentrations of anti-CD3 quantum dots (QD);

FIG. 4 shows $CD4^+$ T cell activation by anti-CD3 QD is Ag-specific and does not occur with empty QD. CFSE dilution in naïve 5C.C7 splenocytes stimulated with no Ag, 50 nM PCC, or 50 nM OVA with or without 18.5 pM anti-CD3 QD or 18.5 pM SA-QD for 3 d;

FIG. 5 shows anti-CD3 QD promote selective, Ag-specific, activation of both $CD4^+$ and $CD8^+$ T cells. Splenocytes from 6.5 TCR-transgenic mice were stimulated with or without HA II peptide for 2 d followed by addition of media, soluble anti-CD3 Ab, or anti-CD3 QD and cultured for another 2 d. CFSE dilutions in $CD4^+6.5-$ gated T cells and $CD4^+6.5^+$ gated T cells from the same cultures are shown;

FIG. 6 shows splenocytes from DO11.10 RAG2$^{-/-}$ (Thy1.2) and WT B10.D2 (Thy1.1) mice were mixed and stimulated with or without OVA II peptide for 1 d followed by addition of media or anti-CD3 QD for another 2 d culture. eFluor 670 dilutions in WT, CD4$^+$ Thy1.1$^+$ gated, and DO11.10, CD4$^+$ Thy1.2$^+$ gated, cells from the same cultures are shown;

FIG. 7 shows splenocytes from clone 4 TCR-transgenic mice were stimulated with or without HA I peptide for 1 d followed by addition of media or anti-CD3 QD and cultured for another 2 d. CFSE dilutions versus CD8$^+$Vb8.1.2$^+$ population are shown;

FIG. 8 shows splenocytes from OT-1 RAG2$^{-/-}$ (Thy1.1) and WT C57BL/6 (Thy1.2) mice were mixed and stimulated with or without OVA I peptide for 1 d followed by addition of media or anti-CD3 QD and cultured for another 2 d. eFluor 670 dilutions in WT (CD8$^+$ Thy1.2$^+$ gated) and OT-1 (CD4$^+$ Thy1.1$^+$ gated) cells from the same cultures are shown;

FIGS. 9A and 9B show anti-CD3 QD enhance cytokine production. (A) IFN-γ production in 6.5 splenocytes stimulated with or without HA II peptide for 2 d, followed by another 4-d culture with or without the presence of anti-CD3 QD. CD4$^+$ gated cells were shown. (B) IFN-γ production by 6.5 splenocytes. Data are representative of three independent experiments;

FIG. 10 shows anti-CD3 QD boost Ag-specific responses of T cells stimulated in vivo. CD4$^+$6.5 splenocytes were transferred to recipient B10.D2 mice. The recipients were immunized s.c. with HA II peptide and CFA. Single-cell suspensions of draining lymph nodes obtained 6 d after vaccination were CFSE labeled and rechallenged with media, soluble anti-CD3, or anti-CD3 QD for another 2 d. Recovery of Ag-specific CD4$^+$6.5$^+$ cells is shown;

FIG. 11 shows proportion of CD4$^+$Vb8.1.2$^+$ cells in single-cell suspensions of draining lymph nodes from B10.D2 (Thy1.2) mice given adoptive transfer of CD4$^+$6.5 splenocytes (Thy1.1) and immunized as in FIG. 10 or with PBS 2 d prior to s.c. boost with media or anti-CD3 QD; single-cell suspensions of draining lymph nodes were obtained 3 d after boost;

FIG. 12 shows B10.D2 mice were given adoptive transfer and immunized as in FIG. 10 1 d prior to s.c. boost with media or anti-CD3 QD. Mice were rechallenged with vaccinia-HA at day 11. Recovery of adoptively transferred cells at day 14 is shown as Thy1.1$^+$ cells;

FIGS. 13A and 13B show IL-2 (A) and IFN-γ (B) production by splenocytes and cells from draining lymph nodes from B10.D2 mice given adoptive transfer and immunized as in FIG. 10 1 d prior to s.c. boost with media or anti-CD3 QD. Mice were rechallenged with vaccinia-HA at day 11. Recovery of adoptively transferred cells at day 14 is shown as Thy1.1$^+$ cells. Splenocytes and cells were stimulated with HA-II peptide for overnight (O/N);

FIGS. 14A-14C show Ag stimulation induces PD-1 clustering on T cells using confocal microscopy. (A) Fresh naïve T cells showed few clusters and a relatively low expression of PD-1 on the surface. (B) After 24 hours of stimulation in vitro with cognate protein, the formation of PD-1 microclusters over the surface of the activated T cells was observed. (C) Even after 6 days of rest, stimulated T cells still demonstrated a high degree of PD-1 clustering on the surface of antigen-experienced T cells;

FIG. 15 shows a schematic representation of how different degrees of PD-1 clustering on the surface of antigen-experienced versus naïve T cells can be exploited to selectively inhibit only the T cells that were recently activated;

FIG. 16 shows that CD8$^+$ T cells incubated with peptide proliferated modestly, while the addition of soluble anti-PD-1 antibody (G4) resulted in enhancement of proliferation. Conversely, the proliferation of CD8$^+$ T cells incubated with peptide was markedly suppressed when Gold-G4 were present in the culture;

FIG. 17 shows that Gold-G4 is able to selectively inhibit antigen-specific T cells response in vivo. Treatment with Gold-G4 led to a decrease in the frequency of vaccine-induced antigen-specific CD8$^+$ Thy1.1$^+$OT-1 T cells compared to that detected from animals given PBS;

FIGS. 18A-18C show: (A) CD8$^+$ T cells incubated with peptide proliferated modestly, while the addition of RMP1-30 resulted in markedly suppression of proliferation. Strikingly, the proliferation of CD8+ T cells incubated with peptide was markedly enhanced when Gold-RMP was present in the culture; (B) OT-1 (Ova-specific TCR transgenic T cells) cells stimulated for 3 days with OVA peptide in combination with no treatment, soluble anti-PD-1 antibodies (clone RMP1-30), or RMP1-30 coated gold nanoparticles and evaluated for proliferation and IFN-γ production These proliferating cells produce robust IFN-γ; and (C) OT-1 cells cultured with Gold-RMP also had a much higher level of IFN-γ secretion compared to cells cultured with medium alone or soluble RMP1-30 as detected by an ELISA assay;

FIGS. 19A and 19B show (A) addition of soluble anti-PD-1 (RMP1-30) markedly suppressed the proliferation of CD4$^+$ T cells incubated with PCC peptide. (B) Proliferation of CD4+ T cells incubated with peptide was enhanced when Gold-RMP were present in the culture (FIG. 19B);

FIG. 20 shows that the tumor burden of mice receiving gold-anti-PD-1 (RMP1-30) showed a markedly slower growth rate compared to control mice ("No Tx") following subcutaneous injection of MC38 mouse colon cells;

FIG. 21 shows the selectivity of anti-PD-1 coated nanoparticles: self reactive T cells (green) do not respond to tumor antigen, fail to cluster PD-1 and thus the anti-PD-1 coated nanoparticle does not inhibit PDL1-induced negative regulation. Alternatively, tumor specific T cells (violet) are activated by tumor antigen, leading to PD-1 clustering leading to the sequestration of PD-1 by anti-PD-1 coated nanoparticles such that PDL1 does not inhibit the anti-tumor T cell response;

FIGS. 22A-22C show that antigen stimulation induces PD-1 clustering: (A) fresh naïve RAG2$^{-/-}$ OT-1 splenocytes stimulated with OVA peptide for 0 h, 24 h and 72 h, or stimulated with peptide for 24 h, washed with PBS, and rested 6 days were stained for PD-1, and imaged by confocal microscopy. Microclusters were classified by size and color-coded using Volocity imaging analysis software. Objects with area <0.01 mm$^2$ were excluded. Scale bars, 2 μm; (B) the average number of microclusters identified on each cell (n≥25); and (C) the average area of each microcluster;

FIG. 23 shows that RMP1-30 anti-PD-1 coated nanoparticles selectively enhance T cell activation: Thy1.1-WT splenocytes were spiked with Thy1.1+, OT-1 T cells then stimulated with peptide alone, peptide+soluble anti-PD-1 or peptide+anti-PD-1 coated cold nanoparticles. As can be seen (top row), the anti-PD-1 coated gold nanoparticles markedly enhance the response to peptide of the Ova-specific T cells, but do not non-specifically activate the Thy1.1-non OT-1 cells;

FIG. 24 shows that the anti-PD-1 coated gold particles enhance T cell responses in vivo (even in the presence of tumor): Mice were injected with B16ova cells and then infected with vaccinia-ova 7 days later+/−anti-PD-1 coated nanoparticles. Thy1.1+ ova specific T cells were quantified 6 days later; and FIG. 25 shows that RMP1-30 coated nanoparticles lead to segregation of TCR and PD-1: OT-1 cells were re-stimulated for 24 hours in the presence of medium, soluble RMP1-30 or RMP1-30 coated gold nanoparticles and stained for PD-1 and CD3, and imaged by confocal microscopy.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides methods and compositions for activation of microclustered receptors on a target cell using nanocarrier-associated ligands, particularly methods and compositions for targeted activation of microclustered receptors on antigen-experienced T cells using nanocarrier-associated antibodies.

I. Methods for Targeted Activation of Microclustered Receptors

On naïve T cells, the antigen (Ag) specific T cell receptor (TCR) is distributed across the surface of the cell in nanoclusters; these nanoclusters oligomerize into microclusters after T cells are activated by Ag (Dustin et al. (2012) *Annu. Rev. Biophys.* 41:543-556; Fahmy et al. (2001) *Immunity* 14:135-143; Zhong et al. (2009) *PLoS ONE* 4:e5945). Clustering promotes the transmission of intracellular signals via the CD3 signaling complex, leading to T cell activation (Anikeeva et al. (2012) *PLoS ONE* 7:e41466; Fernandez-Miguel et al. (1999) *Proc. Natl. Acad. Sci. USA* 96:1547-1552; Grakoui et al. (1999) *Science* 285:221-227; Minguet et al. (2007) *Immunity* 26:43-54). It is also believed to increase the sensitivity for low concentrations of Ag (Schamel et al. (2005) *J. Exp. Med.* 202:493-503) and to generate maximal local signals by providing continuous engagement of TCR/MHC (Huppa et al. (2010) *Nature* 463:963-967). TCR microclusters are observed in both effector and memory cells; their presence correlates with increased sensitivity of Ag-experienced T cells (Kumar et al. (2011) *Immunity* 35:375-387).

It has been estimated that the number of TCRs within a nanocluster, prior to activation, ranges from a single receptor to a cluster of ≥20 (Schamel et al. (2005) *J. Exp. Med.* 202:493-503). Binding experiments indicate that these clusters are 1-3 nm in size (Fahmy et al. (2001) *Immunity* 14:135-143). In contrast, microclusters, which are formed upon T cell activation, have been estimated to be hundreds of nanometers in diameter (Alivisatos (2004) *Nat. Biotechnol.* 22:47-52; Mattoussi et al. (2000) *J. Am. Chem. Soc.* 122:12142-12150) and contain approximately 100 TCR complexes as determined by total internal reflection fluorescence microscopy (Boyle et al. (2011) *Biophys. J.* 101: L57-L59). Furthermore, by employing photoactivated localization microscopy, density domains inside microclusters have been estimated to be 35-70 nm in diameter and contain 7-20 TCRs (Lillemeier et al. (2010) *Nat. Immunol.* 11:90-96). Based on such data, it is reasonable to assume that the distance between two TCR complexes in the microcluster of activated T cells is approximately 20 nm.

A. Method for Selectively Enhancing Activation of Antigen Experienced Cells

Accordingly, in one embodiment, the presently disclosed subject matter is directed to a method for selectively enhancing activation of antigen-experienced cells, the method comprising: a) administering a selected antigen to target cells in an amount sufficient to produce microclustering of ligand-binding receptors on the surface of the target cells, thereby producing antigen-experienced cells comprising microclustered ligand-binding receptors; and b) administering nanocarrier-associated ligands and the selected antigen to a plurality of cells, wherein the plurality of cells comprises antigen-experienced cells and naïve cells; wherein the nanocarrier-associated ligands bind microclustered ligand-binding receptors of the antigen-experienced cells, thereby selectively enhancing activation of the antigen-experienced cells as compared to: i) the binding of free ligands to the microclustered ligand-binding receptors; and/or ii) the binding of nanocarrier-associated ligands to ligand-binding receptors of naïve cells, wherein the naïve cells are non-specifically activated.

As used herein, "activation of antigen-experienced cells" refers to the initiation of a biological response in cells that have been exposed to a selected antigen. For example, antigen stimulation induces the formation of PD-1 microclusters over the surface of T cells as compared to fresh naïve T cells that exhibit few clusters and a relatively low expression of PD-1 on their surfaces.

An "antigen" as used herein is a substance that binds specifically to its respective antibody. Each antibody binds a specific antigenic structure by means of its variable complementarity determining region (CDR) interaction.

As used herein, "naïve cells" are cells that have not been activated by or exposed to the selected antigen.

As used herein, enhancing or stimulating an antigen-specific T cell response includes without limitation inducing, priming, initiating, prolonging, maintaining, amplifying, augmenting, or boosting the response to a selected antigen. In some embodiments, various assays can be utilized to determine whether an antigen-specific T cell response has been stimulated or enhanced in a T cell or group of T cells. In some embodiments, the assay assesses whether or not the cell or group of cells has/have become "activated." In some embodiments, stimulation of an immune response in T cells can be determined by measuring antigen-induced production of cytokines by T cells. In some embodiments, stimulation of an immune response in T cells can be determined by measuring antigen-induced proliferation of T cells. In some embodiments, an immune response in T cells is determined to be stimulated if cellular markers of T cell activation are expressed at different levels (e.g., higher or lower levels) relative to naïve (unstimulated) cells.

In some embodiments of the methods of the presently disclosed subject matter, the antigen-experienced cells and the naïve cells are both T cells, particularly wherein the T cells are selected from the group consisting of CD4+ T cells or CD8+ T cells. "T cells" or "T lymphocytes" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

In other embodiments, selectively enhancing activation of the antigen-experienced cells comprises selectively enhancing an antigen-specific T cell response in the antigen-experienced cells as compared to the naïve cells. In other embodiments, the antigen-specific T cell response comprises enhanced proliferation of the antigen-experienced cells as compared to the naïve cells. In further embodiments, the antigen-specific T cell response comprises promoting the generation and function of specific effector cells from the antigen-experienced cells as compared to the naïve cells.

In still further embodiments, promoting the generation and function of specific effector cells from the antigen-experienced cells comprises increasing the number of antigen-experienced cells producing one or more proteins, particularly wherein the one or more proteins comprise interleukins, and more particularly wherein the interleukins comprise IL-12 or IL-4. Interleukins are a group of cytokines that were first observed to be expressed by white blood cells. The function of the immune system depends in large part on interleukins. The majority of interleukins are synthesized by helper CD4 T lymphocytes, as well as monocytes, macrophages, and endothelial cells. They promote the development and differentiation of T and B lymphocytes and hematopoietic cells. Interleukin 12 (IL-12) is a disulphide-bonded heterodimer consisting of a 35 kDa alpha subunit and a 40 kDa beta subunit. It is involved in the stimulation and maintenance of Th1 cellular immune responses, including the normal host defense against various intracellular pathogens. Interleukin 4 (IL-4) is produced by CD4 T cells specialized in providing help to B cells to proliferate and to undergo class switch recombination and somatic hypermutation.

In still further embodiments, the antigen-specific T cell response comprises enhancing the response of the antigen-experienced cells to a vaccine as compared to the naïve cells, particularly vaccine-induced proliferation of antigen-experienced cells and generation of functional memory cells.

In some embodiments, the ligand-binding receptors are T cell receptors, particularly wherein the ligands are selected from the group consisting of anti-CD3 antibodies, anti-PD-1 antibodies, and functional variants thereof.

The CD3 (cluster of differentiation 3) T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the ζ-chain to generate an activation signal in T lymphocytes. The TCR, ζ-chain, and CD3 molecules together comprise the TCR complex.

Programmed cell death protein 1, also known as PD-1, is a 288 amino acid cell surface protein molecule that in humans is encoded by the PDCD1 gene (Ishida et al. (1992) *EMBO J.* 11:3887; Shinohara et al. (1994) *Genomics* 23:704; U.S. Pat. No. 5,698,520). PD-1 is a member of the immunoglobulin gene superfamily, has an extracellular region containing immunoglobulin superfamily domain, a transmembrane domain, and an intracellular region including an immunoreceptor tyrosine-based inhibitory motif (ITIM; Ishida et al. (1992) *EMBO J.* 11:3887; Shinohara et al. (1994) *Genomics* 23:704).

"Functional variants" of CD-3 and/or PD-1 include functional fragments, functional mutant proteins, and/or functional fusion proteins. A functional variant of a selected polypeptide refers to an isolated and/or recombinant protein or polypeptide which has at least one property, activity and/or functional characteristic of the selected polypeptide. As used herein, the term "activity," when used with respect to a polypeptide, e.g., CD-3 and/or PD-1 includes activities which are inherent in the structure of the wild-type protein.

The term "antibody," also known as an immunoglobulin (Ig), is a large Y-shaped protein produced by B cells that is used by the immune system to identify and neutralize foreign objects such as bacteria and viruses by recognizing a unique portion (epitope) of the foreign target, called an antigen. As used herein, the term "antibody" also includes an "antigen-binding portion" of an antibody (or simply "antibody portion"). The term "antigen-binding portion," as used herein, refers to one or more fragments of an antibody that retain the ability to specifically bind to an antigen (e.g., PD-1 ligand). It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); e.g., Bird et al. (1988) *Science* 242:423-426; Huston et al. (1988) *Proc. Natl. Acad Sci. USA* 85:5879-5883; and Osbourn et al. (1998) *Nature Biotechnology* 16:778). Such single chain antibodies are also intended to be encompassed within the term "antigen-binding portion" of an antibody. Any VH and VL sequences of specific scFv can be linked to human immunoglobulin constant region cDNA or genomic sequences, to generate expression vectors encoding complete IgG polypeptides or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, and the like). Antibodies may also be fully human. Preferably, antibodies of the presently disclosed subject matter bind specifically or substantially specifically to a PD-1 ligand or functional variant thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody," as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody," as used herein, also includes antibodies in which CDR sequences derived from the germline of another mammalian species, such as a mouse, have been grafted onto human framework sequences.

An "isolated antibody," as used herein, is intended to refer to an antibody that is substantially free of other antibodies having different antigenic specificities (e.g., an isolated antibody that specifically binds a PD-1 ligand is substantially free of antibodies that specifically bind antigens other than a PD-1 ligand). Moreover, an isolated antibody may be substantially free of other cellular material and/or chemicals.

An immunogen comprising CD-3, PD-1, or a functional variant thereof typically is used to prepare antibodies by immunizing a suitable subject, (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497; Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), a human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (e.g., Carlson (1988) *Mol. Cell. Biol.* 8:2638-2646; Biocca et al. (1990) *EMBO J.* 9:101-108; Werge et al. (1990) *FEBS Lett.* 274:193-198; Carlson (1993) *Proc. Natl. Acad. Sci. USA* 90:7427-7428; Marasco et al. (1993) *Proc. Natl. Acad. Sci. USA* 90:7889-7893; Biocca et al. (1994) *Biotechnology* (NY) 12:396-399; Chen et al. (1994) *Hum. Gene Ther.* 5:595-601; Duan et al. (1994) *Proc. Natl. Acad. Sci. USA* 91:5075-5079; Chen et ah (1994) *Proc. Natl. Acad. Sci. USA* 91:5932-5936; Beerli et al. (1994) *J. Biol. Chem.* 269: 23931-23936; Beerli et al. (1994) *Biochem. Biophys. Res. Commun.* 204:666-672; Mhashilkar et al. (1995) *EMBO J.* 14:1542-1551; Richardson et al. (1995) *Proc. Natl. Acad. Sci. USA* 92:3137-3141; PCT Publication No. WO 94/02610; and PCT Publication No. WO 95/03832).

Additionally, fully human antibodies could be made against CD3, PD-1, or a functional variant thereof. Fully human antibodies can be made in mice that are transgenic for human immunoglobulin genes, e.g., according to Hogan, et al., "Manipulating the Mouse Embryo: A Laboratory Manual," Cold Spring Harbor Laboratory. Briefly, transgenic mice are immunized with purified PD-1 ligand or functional variant thereof. Spleen cells are harvested and fused to myeloma cells to produce hybridomas. Hybridomas are selected based on their ability to produce antibodies which bind to PD-1 ligand or a functional variant thereof. Fully human antibodies would reduce the immunogenicity of such antibodies in a human.

B. Methods for Treating Infectious Disease or Cancer

In another embodiment, the presently disclosed subject matter is directed to a method for treating infectious disease or cancer in a subject in need thereof, the method comprising administering to the subject: a) a selected antigen in an amount sufficient to produce microclustering of ligand-binding receptors on the surface of target cells in the subject, thereby producing antigen-experienced cells comprising microclustered ligand-binding receptors; and b) nanocarrier-associated ligands in an amount sufficient for the nanocarrier-associated ligands to bind microclustered ligand-binding receptors of the antigen-experienced cells, thereby selectively enhancing activation of the antigen-experienced cells as compared to: i) the binding of free ligands to the microclustered ligand-binding receptors; and/or ii) the binding of nanocarrier-associated ligands to ligand-binding receptors of naïve cells, wherein the naïve cells are non-specifically activated. In some embodiments, the selected antigen and the nanocarrier-associated ligands are administered to the subject concurrently. In other embodiments, the selected antigen and the nanocarrier-associated ligands are administered to the subject sequentially.

The term "administering" as used herein refers to contacting at least a cell with a selected antigen and/or nanocarrier-associated ligands. This term includes administration of the presently disclosed selected antigen and/or nanocarrier-associated ligands to a subject in which the cell is present, as well as introducing the presently disclosed agents into a medium in which a cell is cultured.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments and the like).

In particular embodiments, the subject is suffering from or susceptible to infectious disease or cancer.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, a selected antigen and/or nanocarrier-associated ligands can be administered prophylactically to prevent the onset of a disease, disorder, or condition, or to prevent the recurrence of a disease, disorder, or condition.

The term "effective amount," as in "a therapeutically effective amount," of a selected antigen and/or nanocarrier-associated ligands refers to the amount of the antigen and/or nanocarrier-associated ligands necessary to elicit the desired biological response. As will be appreciated by those of ordinary skill in this art, the effective amount of a selected antigen and/or nanocarrier-associated ligands may vary depending on such factors as the desired biological endpoint, the antigen and/or nanocarrier-associated ligands to be delivered, the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

In one embodiment, the selected antigen is administered in combination with the nanocarrier-associated ligands. As used herein, the term "in combination with" places no limit on the method, mode, form, and the like, of the administration. For example, "in combination with" would include, but is not limited to, simultaneous administration of the selected antigen and the nanocarrier-associated ligands, separately or in a single composition; it would also include sequential administration of the selected antigen and the nanocarrier-associated ligands.

Pharmaceutical compositions of the presently disclosed subject matter may comprise a selected antigen, nanocarrier-associated ligands and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active agents, use thereof in the compositions is contemplated. Supplementary active agents can also be incorporated into the compositions.

A pharmaceutical composition of the presently disclosed subject matter is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols, such as manitol, sorbitol, sodium chloride, in the composition. Prolonged absorption of the injectable compositions can be brought about by including in the composition an agent which delays absorption, for example, aluminum monostearate and gelatin.

Sterile injectable solutions can be prepared by incorporating the active agents (e.g., a selected antigen and/or nanocarrier-associated ligands) in the required amount in an appropriate solvent with one or a combination of ingredients enumerated above, as required, followed by filtered sterilization. Generally, dispersions are prepared by incorporating the active agents into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active agents can be incorporated with excipients and used in the form of tablets, troches, or capsules. Oral compositions can also be prepared using a fluid carrier for use as a mouthwash, wherein the agents in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or agents of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the agents are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

The agents can also be prepared in the form of suppositories (e.g., with conventional suppository bases such as cocoa butter and other glycerides) or retention enemas for rectal delivery.

In one embodiment, modulatory agents are prepared with carriers that will protect the agents against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agents calculated to produce the desired therapeutic effect in association with the required pharmaceutical carrier. The specification for the dosage unit forms of the presently disclosed subject matter are dictated by, and directly dependent on, the unique characteristics of the active agents, the particular therapeutic effect to be achieved, and the limitations inherent in the art of agentsing such an active agents for the treatment of individuals.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents which exhibit large therapeutic indices are preferred. While agents that exhibit toxic side effects can be used, care should be taken to design a delivery system that targets such agents to the site of affected tissue to minimize potential damage to uninfected cells and, thereby, reduce side effects.

The data obtained from the cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized. For any agents used in the method of the presently disclosed subject matter, the therapeutically effective dose can be estimated initially from cell culture assays. A dose can be formulated in animal models to achieve a circulating plasma concentration range that includes the IC50 (i.e., the concentration of the test agents which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered in the form of expressible nucleic acids which encode said agents. Such nucleic acids and compositions in which they are contained, are also encompassed by the present presently disclosed subject matter. For instance, the nucleic acid molecules of the presently disclosed subject matter can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

C. Methods for Selectively Enhancing Activation of Cells Comprising Microclustered Ligand-Binding Receptors In further embodiments, the presently disclosed subject matter is directed to a method for selectively enhancing activation of cells comprising microclustered ligand-binding receptors, the method comprising administering nanocarrier-associated ligands to a plurality of cells, wherein the plurality of cells comprises: a) cells comprising microclustered ligand-binding receptors; and b) cells comprising non-microclustered ligand-binding receptors; wherein the nanocarrier-associated ligands selectively bind microclustered ligand-binding receptors, thereby selectively enhancing activation of cells comprising microclustered ligand-binding receptors as compared to cells comprising non-microclustered ligand-binding receptors. In some embodiments, the cells comprising microclustered ligand-binding receptors comprise cancer cells, particularly wherein the nanocarrier-associated ligands are anti-cancer agents, and wherein selectively enhancing activation of cells comprising microclustered ligand-binding receptors comprises destroying the cancer cells. The anti-cancer agent may be any agent that has an anti-cancer effect on a cell, including an anti-tumour effect, such as a cytotoxic, apoptotic, anti-mitotic anti-angiogenesis or inhibition of metastasis effect. The anti-cancer effect is intended to include inhibition or reduction of tumour cell growth, inhibition or reduction of carcinogenesis, killing of tumour cells, or inhibition or reduction of carcinogenic or tumourogenic properties of a cell, including a tumor cell.

An anti-cancer agent includes a protein, a nucleic acid, a small molecule or a drug. An anti-cancer agent that is a protein may be a peptide, an antibody, a hormone, an enzyme, a growth factor, or a cytokine. An anti-cancer agent that is a nucleic acid may be single stranded or double stranded DNA or RNA, a short hairpin RNA, an siRNA, or may comprise a gene encoding an anti-cancer product. Also included in the scope of anti-cancer agent is a chemotherapeutic agent or an angiogenesis inhibitor. The anti-cancer agent may be an antibody, including a monoclonal antibody, directed against a tumour cell-surface marker, an immunoregulatory peptide, a cytokine or a growth factor. The anti-cancer agent may be Herceptin (trastuzumab) or TNP470 (N-(2-Chloroacetyl)carbamic acid (3R,4S,5S,6R)-5-Methoxy-4-[(2R,3R)-2-methyl-3-(3-methyl-2-buten-1-yl)-2-oxiranyl]-1-oxaspiro[2.5]oct-6-yl ester) an analog of fumagillin, doxorubicin, cisplatin, paclitaxel, daunorubicin, or a mixture thereof.

The anti-cancer agents may include tyrosine kinase inhibitors, or cisplatin, platinum, carboplatin, gemcitabine, paclitaxel, docetaxel, etoposide, vinorelbine, topotecan, or irinotecan. Enzymes inducing apoptosis may include TRAIL-R1, TRAIL-R2 or FasL. Nucleic acid anti-cancer agents may include plasmid DNA (encoding therapeutic proteins) or antisense oligonucleotides (ODNs) or small interfering RNA (siRNA). ODN is a short single stranded DNA, which is complementary to the transcribed mRNA (sense sequence), and hence can bind to this mRNA and prevent it from being translated into the protein inside the cells. Alternatively, ODNs can be targeted to bind to a splicing site of a pre-mRNA, and aimed to modify the exon end of the mRNA. siRNA, on the other hand, is a short double or single stranded RNA, which assembles into endoribonuclease-containing complexes upon entering cells, also known as RNA-induced silencing complex (RISC). These siRNA molecules then unwind inside the RISC, making the complex activated to recognize and splice its mRNA target strands in the cells, and thus down-regulating the expression of the target protein. Similarly micro-RNA capable of inducing apoptosis may be initiated by a specific micro-RNA. The micro-RNA may include: MiR-15, MiR-16, MiR-99a/let7c/MiR-125b2 or other suitable pro-apoptotic micro-RNA.

II. Compositions for Selectively Enhancing Activation of Antigen-Experienced Cells In some embodiments, the presently disclosed subject matter is also directed to a composition for selectively enhancing activation of antigen-experienced cells, the composition comprising: a) a selected antigen in an amount sufficient to produce microclustering of ligand-binding receptors on the surface of target cells, thereby producing antigen-experienced cells comprising microclustered ligand-binding receptors; and b) nanocarrier-associated ligands in an amount sufficient for the nanocarrier-associated ligands to bind microclustered ligand-binding receptors of the antigen-experienced cells, thereby selectively enhancing activation of the antigen-experienced cells as compared to: i) the binding of free ligands to the microclustered ligand-binding receptors; and/or ii) the binding of nanocarrier-associated ligands to ligand-binding receptors of naïve cells, wherein the naïve cells are non-specifically activated. In some embodiments, the antigen-experienced cells and the naïve cells are both T cells, particularly wherein the T cells are selected from the group consisting of $CD4^+$ T cells or $CD8^+$ T cells. In other embodiments, the antigen is a protein or peptide. In some embodiments, the ligand-binding receptors are T cell receptors, particularly wherein the ligands are selected from the group consisting of anti-CD3 antibodies, anti-PD-1 antibodies, and functional variants thereof.

The compositions and methods of the presently disclosed subject matter comprise nanocarriers. A nanocarrier can be, but is not limited to, one or a plurality of lipid nanoparticles, polymeric nanoparticles, metallic nanoparticles, carbon nanoparticles, surfactant-based emulsions, dendrimers, and/or nanoparticles that are developed using a combination of nanomaterials such as lipid-polymer nanoparticles.

The scaffold of the nanocarrier (and which the agents disclosed herein may be associated with and/or bound to) can be composed of polymer and/or non-polymer molecules. Accordingly, the nanocarrier scaffold can be protein-based, nucleic acid based, or carbohydrate-based. The scaffold, in some embodiments, is macromolecular. In some embodiments, the scaffold is composed of amino acids or nucleic acids. In some embodiments, the scaffold is composed of crosslinking chains of molecules, such as nucleic acids. In some embodiments, the scaffold is composed of RNAi crosslinking chains. In some embodiments, the scaffold is polyamino-based. A nanocarrier can be, but is not limited to, one or a plurality of lipid-based nanoparticles, polymeric nanoparticles, metallic nanoparticles, surfactant-based emulsions, dendrimers, and/or nanoparticles that are developed using a combination of nanomaterials such as lipid-polymer nanoparticles.

In some embodiments, the nanocarrier is composed of one or more polymers. In some embodiments, the one or more polymers is a water soluble, non-adhesive polymer. In some embodiments, polymer is polyethylene glycol (PEG) or polyethylene oxide (PEO). In some embodiments, the polymer is polyalkylene glycol or polyalkylene oxide. In some embodiments, the one or more polymers is a biodegradable polymer. In some embodiments, the one or more polymers is a biocompatible polymer that is a conjugate of a water soluble, non-adhesive polymer and a biodegradable polymer. In some embodiments, the biodegradable polymer is polylactic acid (PLA), poly(glycolic acid) (PGA), or poly (lactic acid/glycolic acid) (PLGA). In some embodiments, the nanocarrier is composed of PEG-PLGA polymers.

In some embodiments, the nanocarrier is formed by self-assembly. Self-assembly refers to the process of the formation of a nanocarrier using components that will orient themselves in a predictable manner forming nanocarriers predictably and reproducably. In some embodiments, the nanocarriers are formed using amphiphillic biomaterials which orient themselves with respect to one another to form nanocarriers of predictable dimension, constituents, and placement of constituents. According to the invention, the amphiphillic biomaterials may have attached to them immunomodulatory agents, immunostimulatory agents and/or targeting agents such that when the nanocarriers self assemble, there is a reproducible pattern of localization and density of the agents on/in the nanocarrier.

In some embodiments, the nanocarrier is a nanoparticle. In some embodiments, the nanoparticle is self-assembled.

The nanocarriers of the compositions provided herein, in some embodiments, have a mean geometric diameter that is less than 100 nm. In some embodiments, the nanocarriers have mean geometric diameter that is greater than 10 nm but less than 100 nm. In some embodiments, the mean geometric diameter of a population of nanocarriers is about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, or 95 nm. In some embodiments, the mean geometric diameter is between 10-100 nm, 20-90 nm, 30-80 nm, or 40-70 nm.

A variety of different nanocarriers can be used in accordance with the presently disclosed subject matter. In some embodiments, nanocarriers are spheres or spheroids. In some embodiments, nanocarriers are flat or plate-shaped. In some embodiments, nanocarriers are cubes or cuboids. In some embodiments, nanocarriers are ovals or ellipses. In some embodiments, nanocarriers are cylinders, cones, or pyramids. Nanocarriers may be solid or hollow and may comprise one or more layers. In some embodiments, each layer has a unique composition and unique properties relative to the other layer(s). To give but one example, nanocarriers may have a core/shell structure, wherein the core is one layer (e.g., a polymeric core) and the shell is a second layer (e.g., a lipid bilayer or monolayer). Nanocarriers may comprise a plurality of different layers. In some embodiments, one layer may be substantially cross-linked, a second layer is not substantially cross-linked, and so forth.

In some embodiments, nanocarriers may optionally comprise one or more lipids. In some embodiments, a nanocarrier is a liposome. In some embodiments, a nanocarrier comprises a lipid bilayer. In some embodiments, a nanocarrier comprises a lipid monolayer. In some embodiments, a nanocarrier is a micelle. In some embodiments, a nanocarrier comprises a core of a polymeric matrix surrounded by a lipid layer (e.g., lipid bilayer, lipid monolayer, and the like). In some embodiments, a nanocarrier comprises a non-polymeric core (e.g., metal particle, carbon particle, quantum dot, ceramic particle, bone particle, viral particle, and the like) surrounded by a lipid layer (e.g., lipid bilayer, lipid monolayer, and the like). In other embodiments, a nanocarrier comprises one or more polymers. In some embodiments, a polymeric matrix can be surrounded by a coating layer (e.g., liposome, lipid monolayer, micelle, and the like).

A wide variety of polymers and methods for forming polymeric matrices therefrom are known in the art of drug delivery. In general, a polymeric matrix comprises one or more polymers. Any polymer may be used in accordance with the presently disclosed subject matter. Polymers may be natural or unnatural (synthetic) polymers. Polymers may be homopolymers or copolymers comprising two or more monomers. In terms of sequence, copolymers may be random, block, or comprise a combination of random and block sequences. Polymers in accordance with the presently disclosed subject matter may be organic polymers. In some embodiments, the polymers are dendritic polymers or blends of polymers.

Examples of polymers include polyethylenes, polycarbonates (e.g., poly(1,3-dioxan-2one)), polyanhydrides (e.g., poly(sebacic anhydride)), polyhydroxyacids (e.g., poly(β-hydroxyalkanoate)), polypropylfumerates, polycaprolactones, polyamides (e.g., polycaprolactam), polyacetals, polyethers, polyesters (e.g., polylactide, polyglycolide), poly(orthoesters), polycyanoacrylates, polyvinyl alcohols, polyurethanes, polyphosphazenes, polyacrylates, polymethacrylates, polyureas, polystyrenes, and polyamines.

In some embodiments, nanocarriers comprise immunomodulatory agents embedded within reverse micelles. To give but one example, a liposome nanocarrier may comprise hydrophobic immunomodulatory agents embedded within the liposome membrane, and hydrophilic immunomodulatory agents embedded with reverse micelles found in the interior of the liposomal nanocarrier.

In some embodiments, a nanocarrier does not include a polymeric component. In some embodiments, nanocarriers comprise metal particles, carbon particles, quantum dots, ceramic particles, bone particles, viral particles, and the like. In some embodiments, the selected ligand is associated with the surface of such a non-polymeric nanocarrier. In some embodiments, a non-polymeric nanocarrier is an aggregate of non-polymeric components, such as an aggregate of metal atoms (e.g., gold atoms). In some embodiments, the selected ligand is associated with the surface of, encapsulated within, surrounded by, and/or dispersed throughout an aggregate of non-polymeric components.

In some embodiments, nanocarriers may optionally comprise one or more amphiphilic entities (i.e., entities that possess both hydrophilic and hydrophobic properties). In some embodiments, an amphiphilic entity can promote the production of nanocarriers with increased stability, improved uniformity, or increased viscosity. In some embodiments, a nanocarrier comprises one or more nanoparticles associated with the exterior surface of and/or encapsulated within the nanocarrier.

Nanocarriers may be prepared using any method known in the art. For example, particulate nanocarrier formulations can be formed by methods such as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, as well as other methods well known to those of ordinary skill in the art. Alternatively or additionally, aqueous and organic solvent syntheses for monodisperse semiconductor, conductive, magnetic, organic, and other nanoparticles may be utilized.

The presently disclosed subject matter is also directed to nanocarrier-associated ligands. As used herein, the term "associated with" refers to the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g., charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, etc.). For example, in some embodiments, a selected ligand may be covalently associated with a nanocarrier. In some embodiments, a selected ligand may be non-covalently associated with a nanocarrier. For example, the entity may be associated with the surface of, encapsulated within, surrounded by, and/or distributed throughout a lipid bilayer, lipid monolayer, polymeric matrix, and the like, of a nanocarrier.

Accordingly, nanocarrier-associated ligands may be on the surface of the nanocarrier, encapsulated within the nanocarrier, or both. In some embodiments, the ligand is on the surface of the nanocarrier at a density which activates T cell receptors. In some embodiments, the ligand is associated with the nanocarrier. In some embodiments, the ligand is covalently associated with the nanocarrier. In some embodiments, the ligand is non-covalently associated with the nanocarrier. In some embodiments, the ligand is a small molecule.

Selected antigens contemplated as useful in the compositions and methods disclosed herein include, but are not limited to proteins, peptides, polypeptides and derivatives thereof, as well as non-peptide macromolecules. Such a derivative can be prepared by any method known to those of ordinary skill in the art and can be assayed by any means known to those of ordinary skill in the art. A general term for these antigens, which are to be recognized or targeted by the immune response, is target-associated antigen (TAA). The terms "target-associated antigen" and "selected antigen" are interchangeable as used herein.

Accordingly, in some embodiments, antigens for use in the presently disclosed subject matter include, but are not limited to, a universal T cell antigen, an infectious disease antigen, and a cancer antigen.

As used herein, the term "universal T cell antigen" refers to a T cell antigen that can promote T cell help and enhance an immune response to a completely unrelated antigen. Universal T cell antigens include tetanus toxoid, as well as one or more peptides derived from tetanus toxoid, Epstein-Barr virus, or influenza virus. Universal T cell antigens also include a component of influenza virus, such as hemagglutinin, neuraminidase, or nuclear protein, or one or more peptides derived therefrom.

In some embodiments, the selected antigen is from an infectious agent. In some embodiments, the infectious agent is a bacterium, fungus, virus, protozoan, or parasite. In some embodiments, the infectious disease antigen is a viral antigen. In some embodiments, the viral antigen is an antigen from a pox virus, smallpox virus, ebola virus, marburg virus, dengue fever virus, influenza virus, parainfluenza virus, respiratory syncytial virus, rubeola virus, human immunodeficiency virus, human papillomavirus, varicella-zoster virus, herpes simplex virus, cytomegalovirus, Epstein-Barr virus, JC virus, rhabdovirus, rotavirus, rhinovirus, adenovirus, papillomavirus, parvovirus, picornavirus, poliovirus, virus that causes mumps, virus that causes rabies, reovirus, rubella virus, togavirus, orthomyxovirus, retrovirus, hepadnavirus, coxsackievirus, equine encephalitis virus, Japanese encephalitis virus, yellow fever virus, Rift Valley fever virus, hepatitis A virus, hepatitis B virus, hepatitis C virus, hepatitis D virus, or hepatitis E virus.

In some embodiments, the selected antigen is a cancer antigen. Cancer antigens include, but are not limited to, differentiation antigens, embryonic antigens, cancer-testis antigens, antigens of oncogenes and mutated tumor-suppressor genes, unique tumor antigens resulting from chromosomal translocations, viral antigens, and others that can be apparent presently or in the future to one of skill in the art.

In other embodiments, protein antigens that can be employed in the disclosed methods and compositions include, but are not limited to: differentiation antigens such as, for example, MART-1/MelanA (MART-I), gp100 (Pmel 17), tyrosinase, TRP-1, TRP-2 and tumor-specific multilineage antigens such as, for example, MAGE-1, MAGE-3, BAGE, GAGE-1, GAGE-2, p15; overexpressed embryonic antigens such as, for example, CEA; overexpressed oncogenes and mutated tumor-suppressor genes such as, for example, p53, Ras, HER-2/neu; unique tumor antigens resulting from chromosomal translocations such as, for example, BCR-ABL, E2A-PRL, H4-RET, IGH-IGK, MYL-RAR; and viral antigens, such as, for example, the Epstein Barr virus antigens EBVA and the human papillomavirus (HPV) antigens E6 and E7. Other protein antigens can include, for example: TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, β-Catenin, CDK4, Mum-1, p15, p16, 43-9F, 5T4, 791Tgp72, alpha-fetoprotein, β-HCG, BCA225, BTAA, CA 125, CA 15-3\CA 27.29\BCAA, CA 195, CA 242, CA-50, CAM43, CD68\KP1, CO-029, FGF-5, G250, Ga733\EpCAM, HTgp-175, M344, MA-50, MG7-Ag, MOV18, NB/70K, NY-CO-1, RCAS1, SDCCAG16, PLA2, TA-90\Mac-2 binding protein\cyclophilin C-associated protein, TAAL6, TAG72, TLP, and TPS. These protein-based antigens are known and available to the skilled artisan both in the literature or commercially.

In further embodiments, peptide antigens of 8-15 amino acids in length are contemplated. Such a peptide can be an epitope of a larger antigen, i.e., it is a peptide having an amino acid sequence corresponding to the site on the larger molecule that is presented by MHC/HLA molecules and can be recognized by, for example, an antigen receptor or T cell receptor. These smaller peptides are available to one of skill in the art and can be obtained, for example, by following the teachings of U.S. Pat. Nos. 5,747,269 and 5,698,396; and PCT Application No. PCT/EP95/02593 (published as WO 96/01429) and PCT Application No. PCT/DE96/00351 (published as WO 96/27008). Additional approaches to epitope discovery are described in U.S. Pat. Nos. 6,037,135 and 6,861,234.

III. General Definitions

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

As used herein, the term "modulate" includes up-regulation and down-regulation, e.g., enhancing or inhibiting a response. As used herein, the term "inhibit" includes the decrease, limitation, or blockage, of, for example a particular action, function, or interaction.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

It was hypothesized that the difference in TCR clustering between naïve and recently activated T cells could be exploited to selectively boost Ag-specific responses. To test this hypothesis, mAb to CD3, a general T cell activator, bound to quantum dots (QD) was used (Alivisatos (2004) *Nat. Biotechnol.* 22:47-52; Bruchez et al. (1998) *Science* 281:2013-2016; Holtz (2005) *Methods Mol. Biol.* 303:1-17; Michalet et al. (2005) *Science* 307:538-544). Anti-CD3-coated Qdots 605 (anti-CD3 QD; Invitrogen) are approximately 18 nm in diameter and coupled to multiple anti-CD3

Abs, which are potent T cell agonists. It was demonstrated that anti-CD3 constrained on the surface of a nanoparticle selectively activated only T cells that were Ag-experienced and, in contrast to soluble anti-CD3, did not activate naïve T cells.

Methods

Microscopy:

Cells were fixed by 2% formaldehyde and stained with rabbit anti-mouse CD3-γ (Santa Cruz Biotechnology) overnight and goat anti-rabbit DyLight 488 (Jackson ImmunoResearch Laboratories) for 2 h. Cells were then mounted with Prolong Gold Anti-fade reagent (Invitrogen) and imaged with an upright fluorescence microscope with 710NLO-Meta confocal module (AxioExaminer; Zeiss) with a 633/1.2W C-Apo objective. Microclusters were identified using the "Find objects using intensity (0.21044)" and "Separate touching objects (object size guide 0.08 μm$^2$)" functions of Volocity imaging analysis software (PerkinElmer). Data were acquired with Zen imaging software (Zeiss) and analyzed with Volocity analysis software (PerkinElmer).

Mice:

Mice were kept in accordance with guidelines of the Johns Hopkins University Institutional Animal Care and Use Committee. 5C.C7 TCR-transgenic RAG2$^{-/-}$ mice and DO11.10 TCR-transgenic RAG2$^{-/-}$ mice (Thy1.2$^+$, Kd; hemagglutinin [HA]-specific) were from Taconic Farms. 6.5 TCR-transgenic (Thy1.1$^+$, K$^d$; HA-specific) mice, B10.D2 (Thy1.1$^+$, Kd) mice, clone 4 TCR transgenic (Thy1.1$^+$, Kd; HA-specific) mice, OT-1 TCR transgenic RAG2$^{-/-}$ (Thy1.1$^+$, Kb; HA-specific) mice, and B10.D2 (Thy1.2$^+$, Kd) mice were a gift from Charles Drake (Departments of Oncology, Immunology and Urology, School of Medicine, Johns Hopkins University, Baltimore, Md.). C57BL/6 (Thy1.2$^+$, K$^b$) mice were obtained from The Jackson Laboratory.

Reagents and Abs:

Hamster anti-mouse CD3 (145-2C11) Qdot 605 and Qdot 655 streptavidin (SA) conjugate were purchased from Invitrogen. Abs against the following proteins were purchased from BD Biosciences: CD4 (GK1.5), CD8a (53-6.7), Thy1.1 (OX-7), Thy1.2 (53-2.1), Vb8.1/8.2 (MR5-2), IFN-γ (XMG1.2), and IL-4 (11B11). Biotin-labeled Abs against 6.5 TCR and stimulatory anti-CD3 (145-2C11) Abs as well as neutralizing anti-IL-4 (11B11) and anti-IFN-γ (XMG1.2) Abs were purified from hybridoma supernatants prepared in-house. Neutralizing anti-IL-12p40 (C17.8) Abs were from eBioscience. Other regents used: CFSE cell proliferation kit (Invitrogen), eFluor 670 cell proliferation dye (eBioscience), fluorophore conjugated SA (BD Biosciences), IL-2, IL-7, IFN-γ, IL-12 p40, and IL-4 cytokines (all from PeproTech), PCC protein and OVA protein (Sigma-Aldrich), HA class II peptide (SFERFEIFPKE, SEQ ID NO:1), HA class I peptide (IYSTVASSL) (both from Johns Hopkins Synthesis and Sequencing Facility), OVA class II peptide (ISQAVHAAHAEINEAGR, SEQ ID NO:2), OVA class I peptide (SIINFEKL, SEQ ID NO:3) (both from AnaSpec), and Imject Freund's Complete Adjuvant (Thermo Scientific)

Flow Cytometry and Intracellular Staining:

All experiments were performed on a BD FASCalibur (BD Biosciences) and analyzed using FlowJo analysis software (Tree Star). Brefeldin A (GolgiPlug; BD Biosciences) or monensin (GolgiStop; BD Biosciences) was used for cytokine staining. Cells were surface stained and underwent fixation/permeabilization followed by staining for intracellular proteins in Perm/Wash Buffer (reagents all from BD Biosciences). Gates were set appropriately with unstimulated and controls. Voltages were determined from unstained controls.

Proliferation and ELISA:

Proliferation was measured by dilution of CFSE or eFluor 670 cell proliferation dyes. Cells were labeled according to the manufacturer's protocol. The cytokines IFN-γ and IL-4 were measured in supernatants by ELISA as described by the manufacturer (eBioscience).

Cell Culture:

Unless otherwise stated, splenocytes were cultured in 50% RPMI 1640/50% EHAA media supplemented with 10% heat-inactivated low-LPS FBS, 1% penicillin/streptomycin, and 1% glutamine. APCs were from the non-CD4$^+$, column-bound fraction of CD4$^+$ T cell isolation. For Th1 and Th2 cultures, splenocytes were stimulated in media supplemented with 5 mM PCC and different skewing cytokines and Abs for 48 h. Skewing conditions were as follows: Th1: IL-12 (5 ng/ml), IFN-γ (100 ng/ml), and anti-IL-4 (100 μg/ml); and Th2: IL-4 (1 ng/ml), anti-IL-12 (100 μg/ml), and anti-IFN-γ (100 μg/ml).

Adoptive Transfer:

For adoptive transfer experiments, 6.5 TCR-transgenic mice were sacrificed via $CO_2$ asphyxiation. Spleens and lymph nodes were collected and homogenized, and RBCs were lysed. CD4$^+$ T cells were purified using Miltenyi magnetically labeled beads (Miltenyi Biotec) according to the manufacturer's protocol. Cells were then washed and resuspended with PBS for i.v. injections. Typically, 1-5×10$^6$ cells were injected per mouse in 0.2 ml PBS by retro-orbital i.v. injection.

Results

Ag Recognition Leads to TCR Clustering:

Emerging studies reveal that after Ag recognition, there is clustering of TCRs not only at the T cell-APC interface but also on the whole surface of the T cell (Huppa et al. (2010) *Nature* 463:963-967). Confocal microscopy was employed to image the distribution of TCRs on T cells before and after Ag exposure. Imaging was performed 1 mm below the top of the cell, trading off sharpness for the largest area of membrane in a single image. It has been reported that membrane molecules remain mobile after fixation (Tanaka et al. (2010) *Nat. Methods* 7:865-866), and the observed clustering could be amplified by the Ab used for staining. However, the observed clustering differences between naïve and primed cells are consistent with those on live cells.

Naïve RAG2$^{-/-}$ CD4$^+$5C.C7 TCR-transgenic T cells, stained for the TCR signaling complex using purified anti-CD3 and Alexa 488-labeled secondary Ab, showed few clusters and a relatively uniform distribution of TCR on the surface (FIG. 1A). After 24 h of stimulation in vitro with 0.05 μM PCC protein, the formation of TCR microclusters over the surface of the activated T cells was observed (FIG. 1B). To determine whether these microclusters persisted, 5C.C7 cells stimulated in vitro with 0.05 μM PCC protein were then rested in media supplemented with 100 ng/ml IL-2 and 10 ng/ml IL-7 without Ag for another 6 d. At this time point, 6 d after the encounter with Ag, the TCR microclusters were still present (FIG. 1C).

To further quantify the numbers of microclusters on T cells, images of at least 25 cells for each condition were collected and microclusters were identified using the Volocity software (PerkinElmer) (FIG. 1D-F). Fresh, naïve 5C.C7 cells had an average of 15 microclusters on a single imaging slice. In contrast, there was a marked increase in the number of microclusters, to an average of 50 per cell, after 24 h of stimulation. Similarly, after resting for 6 d, an average of 35 microclusters on the surface of the cells were still observed (FIG. 1G). The average area of the microclusters on the activated cells was 0.1255 µm². The size of the microclusters decreased to 0.0844 µm² after 6 d of rest; however, their size remained larger than those observed on the naïve T cells, which was 0.0667 µm² (FIG. 1H). The total amount of TCRs expressed on the surface of the naïve and 6-d activated T cells, as determined by mean fluorescence intensity, was similar (FIG. 1I). Thus, although the overall number of TCRs on the surface of naïve and recently activated T cells was similar, the size and intensity of TCR microclusters differentiated Ag-experienced 5C.C7 T cells from naïve cells.

Constraining Anti-CD3 Abs on Nanoparticles Selectively Activated Ag-Experienced CD4+ T Cells:

Soluble anti-CD3 activated all T cells regardless of their Ag specificity by cross linking the TCR-CD3 signaling machinery (Meuer et al. (1984) *Proc. Natl. Acad. Sci. USA* 81:1509-1513; Van Wauwe et al. (1980) *J. Immunol.* 124: 2708-2713). Without wishing to be bound to any one particular theory, it was postulated that the different degrees of TCR clustering on the surface of Ag-experienced versus naïve T cells could be exploited to selectively activate only the T cells that had previously engaged Ag (FIG. 2A, 2B). It was further reasoned that in general, the cross linking ability of anti-CD3 when constrained to a nanoparticle would be limited when the TCRs were scattered across the surface of the cell, as is the case for naïve T cells, but that the anti-CD3 QD could engage the TCR in the microclusters that develop after T cell activation.

To this end, naïve 5C.C7 splenocytes were incubated in vitro with media or PCC protein together with anti-CD3 QD for 72 h and evaluated for proliferation. T cells that were not previously activated by Ag failed to proliferate in response to the anti-CD3 QD even at the highest concentration, but responded perfectly well to soluble anti-CD3. T cells incubated with low-dose peptide proliferated modestly, whereas the addition of anti-CD3 QD resulted in markedly enhanced proliferation. This selective enhancement also increased with increasing amounts of anti-CD3 QD (FIG. 3). In addition, the ability of the anti-CD3 QD to enhance proliferation was maintained even if the Ag from the culture was removed.

It was hypothesized that TCR clustering on the surface of previously activated T cells enables them to be stimulated by the anti-CD3-coated QD. To test this hypothesis, 5C.C7 cells were stimulated with PCC protein for 2 d, rested in IL-2 and IL-7 for 7 d, and then were CFSE labeled and restimulated with anti-CD3 QD and fresh APCs. T cells that had seen Ag 6 d earlier proliferated vigorously in response to 1 nM of anti-CD3 QD but did not respond to fresh APCs alone. Also, naïve 5C.C7 cells responded minimally to the same concentration of anti-CD3 QD (data not shown). Thus, Ag-experienced T cells, for which TCR were clustered, were responsive to anti-CD3 QD, whereas T cells that had yet to see their Ag (and had most TCR diffusely distributed) were unresponsive.

The ability of anti-CD3 QD to selectively enhance the proliferation of Ag-experienced T cells was Ag-specific. PCC-specific 5C.C7 T cells were incubated with specific Ag, PCC, or with control OVA and then assayed for their ability to respond to the anti-CD3 QD. After 72 h, naïve 5C.C7 cells responded minimally to anti-CD3 QD without the presence of peptide (FIG. 4). 5C.C7 T cells coincubated with OVA Ag failed to respond to 18.5 pM anti-CD3 QD (FIG. 4). In addition, stimulation of Ag-experienced T cells was not a property of unmodified QD, because SA-coated QD lacking anti-CD3 failed to stimulate proliferation of the Ag-experienced 5C.C7 T cells (FIG. 4).

Constraining Anti-CD3 Abs on Nanoparticles Selectively Activates Both CD4+ and CD8+ T Cells:

First, the experiments were repeated with splenocytes from RAG+/+6.5 TCR-transgenic mice. The 6.5-transgenic TCR is specific for class II HA peptide. However, because these mice are wild-type (WT) for the RAG gene, only 10-20% of the CD4+ T cells express the transgenic TCR. The remaining cells, which are negative for the transgenic TCR (6.5−), express TCR with other specificities. This allows simultaneous evaluation of the specificity of anti-CD3 QD for Ag-specific and endogenous T cells in a single culture. The splenocytes were stimulated with HA II peptide for 48 h followed by the addition of anti-CD3 QD or soluble anti-CD3. Proliferation was analyzed 3 d after addition of anti-CD3 QD. Both 6.5+ and 6.5− T cells proliferated in response to 23 nM soluble anti-CD3 regardless of whether the cells were preincubated with HA peptide (FIG. 5). In contrast, none of the 6.5+ or 6.5− T cells proliferated in response to 8.7 nM anti-CD3 QD alone without HA peptide. Low-dose HA II peptide, as expected, only stimulated the 6.5+ T cells. The addition of anti-CD3 QD to such cultures led to a marked enhancement of proliferation of the 6.5+ T cells but not of the 6.5− T cells (FIG. 5). There were similar concentrations of anti-CD3 in both culture conditions: 23 nM in soluble Ab and ~45 nM in anti-CD3 QD, assuming there are 5-10 Abs on a QD (Mattoussi et al. (2000) *J. Am. Chem. Soc.* 122:12142-12150). Because the amounts of anti-CD3 Abs are similar, the enhancement of activation by anti-CD3 QD does not reflect a large difference in Ab available for cross-linking TCR, but rather the difference between the cross-linking capacity of soluble Ab molecules and that of Abs constrained onto nanoparticles.

A second experimental system was next tested for the selectivity of anti-CD3 QD in activating Ag-specific CD4+ T cells. Splenocytes from class II OVA-specific DO11.10 RAG2−/− (Thy1.2) mice and WT B10.D2 (Thy1.1) mice, which share the same H-2d background, were cocultured with or without class II OVA peptide. Anti-CD3 QD or media was added to the culture 1 d later for an additional 2 d. Without the addition of OVA peptide, neither B10.D2 nor DO11.10 CD4+ cells proliferated (FIG. 6). The addition of class II OVA peptide led to the proliferation of only the Ag-specific DO11.10 cells. The addition of anti-CD3 QD to the OVA-treated cultures led to the enhanced proliferation of the DO11.10 T cells but did not stimulate the B10.D2 CD4+ T cells (FIG. 6).

Clustering of TCRs upon Ag-induced activation has also been shown for CD8+ T cells (Boyle et al. (2011) *Biophys. J.* 101:L57-L59). It was found that anti-CD3-coated QD also selectively enhanced the activation of CD8+ T cells. RAG CD8+ clone 4 TCR-transgenic T cells, specific for class I HA peptide, were stimulated with 10 nM of HA I for 24 h. Anti-CD3 QD were then added into the culture to a final concentration of 10 nM 2 d before the cells were harvested. As was observed with CD4+ T cells, anti-CD3 QD alone did not induce proliferation in the absence of Ag. However, coculture of HA class I peptide with the anti-CD3-coated QD led to a marked enhancement of the Ag-specific (Vb8.2+) CD8+ T cells (FIG. 7). Thus, anti-CD3 QD could also selectively enhance the activation of Ag-specific CD8+ T cells.

The ability of anti-CD3-coated QD to selectively enhance CD8+ T cell activation in cultures containing T cells of mixed specificity was next tested. T cells from OVA-specific RAG2−/− CD8+OT-1 (Thy1.1+) TCR-transgenic mice were mixed with T cells from WT C57BL/6 (Thy1.2) mice. The cells were cultured with or without class I OVA peptide in the presence and absence of anti-CD3 QD. Anti-CD3 QD alone or media failed to induce T cell proliferation in any of the CD8$^+$ T cells (FIG. 8). In the presence of class I OVA peptide, only the Ag-specific OT-1 cells proliferated. The addition of anti-CD3 QD to such cultures led to the enhanced activation of the OT-1 CD8$^+$ T cells but not the other CD8$^+$ T cells (FIG. 8). Thus, anti-CD3 QD have the ability to selectively enhance the activation of Ag-specific CD8$^+$ T cells as well as CD4$^+$ T cells.

Anti-CD3 QD Enhanced Effector Generation and Function:

Thus far, the ability of anti-CD3 QD to enhance the proliferation of CD4$^+$ and CD8$^+$ T cells has been demonstrated. Whether the anti-CD3 QD could promote the generation of specific CD4$^+$ effector cells was next tested. Splenocytes from CD4$^+$6.5 TCR-transgenic mice were stimulated in vitro with class II HA peptide for 48 h. Anti-CD3 QD were then added to the culture and cells incubated for another 4 d. In these long-term cultures, the addition of anti-CD3 QD led to an increase in the number of IFN-γ-producing 6.5$^+$ T cells (FIG. 9A). This increase in IFN-γ-secreting cells was also reflected in the amount of IFN-γ secreted into the supernatant as measured by ELISA (FIG. 9B).

Anti-CD3 QD selectively enhanced effector cell generation under specific Th skewing conditions (FIG. 5C). Naïve 5C.C7 splenocytes were incubated with PCC peptide under conditions that would promote the generation of either Th1 (IFN-γ plus IL-12 plus anti-IL-4 Ab) or Th2 (IL-4 plus anti-IFN-γ Ab plus anti-IL-12 Ab) effector cells for 2 d. On the third day, the cells were incubated with different concentrations of anti-CD3 QD and then assayed for both proliferation and cytokine production. As expected, anti-CD3 QD enhanced the proliferation of Ag-activated T cells in both Th1 and Th2 conditions (FIG. 5D). Furthermore, the addition of the anti-CD3 QD enhanced the production of IFN-γ in the cells activated under Th1 conditions and production of IL-4 in the cells activated under Th2 conditions. Thus, the anti-CD3 QD enhanced both proliferation and cytokine production in Ag-experienced CD4$^+$ effector cells.

Anti-CD3 QD Boosted Responses to Vaccines In Vivo:

Next, it was determined whether activation of T cells in vivo rendered them susceptible to activation by anti-CD3 QD. 6.5$^+$ Thy1.1$^+$CD4$^+$ T cells were transferred into WT B10.D2 Thy1.2$^+$ mice, which were then injected with class II HA peptide mixed with CFA. Six days later, draining lymph nodes were harvested. The harvested cells were CFSE labeled and then cultured in media only or with anti-CD3 QD. After 3 d of in vitro restimulation with anti-CD3 QD, it was observed that only the 6.5$^+$CD4$^+$ T cells responded. That is, the anti-CD3 QD only stimulated the lymph node T cells that had previously encountered Ag in vivo (FIG. 10). Both 6.5$^+$ and 6.5- T cells proliferated in positive control cultures, with soluble anti-CD3 (FIG. 6B) and abrogated specificity. Thus, in vivo-activated Ag-specific T cells were as responsive to anti-CD3 QD to cells that were activated in vitro.

Finally, it was determined whether anti-CD3 QD could enhance the response to a vaccine in vivo. Again, 6.5$^+$ Thy1.1$^+$CD4$^+$ T cells were adoptively transferred into WT B10.D2 Thy1.2$^+$ mice, which were then vaccinated s.c. with PBS or class II HA peptide with CFA to generate newly activated 6.5$^+$ T cells. Two days later, mice were injected with PBS or anti-CD3 QD at the same site. Three days later, draining lymph nodes were harvested, and the frequency of Ag-specific CD4$^+$Vb8.1.2$^+$ cells was evaluated. Treatment with anti-CD3 QD led to an increase in the frequency of vaccine-induced Ag-specific CD4$^+$Vb8.1.2$^+$ T cells in the draining lymph nodes compared with the frequency in nodes of animals given PBS (FIG. 11), but did not lead to widespread activation of endogenous memory T cells. Thus, the sequenced administration of Ag and anti-CD3 QD enhanced the initial vaccine-induced expansion of Ag-specific T cells in vivo. To expand these findings, a similar experiment was performed to determine if the addition of anti-CD3 QD could enhance the generation of memory cells. Mice were vaccinated with peptide and then injected with PBS or anti-CD3 QD 1 d later. After an additional 11 d, the mice were infected with vaccinia virus that expresses HA peptide. It was observed that mice which received the peptide (day 0) followed by the anti-CD3 QD (day 1) had an increased recall response when challenged with vaccinia virus that expresses HA peptide administered on day 12 (FIG. 12). In addition, Ag-specific T cells from the anti-CD3 QD-treated mice had higher IFN-γ and IL-2 production than controls (FIG. 13A, 13B). These results were consistent with the hypothesis that the sequenced administration of Ag and anti-CD3 QD enhance the generation of functional memory cells. Without being bound by any particular theory, these data also argue against the possibility that enhanced proliferation of T cells induced by anti-CD3 QD results in cell death after the initial burst of proliferation.

Discussion

Nanoparticles have been explored for various applications not only because of their miniature size but also because of their relatively large surface area, which allows immobilization of multiple ligands (Cho et al. (2011) *Nat. Nanotechnol.* 6:675-682; Sun et al. (2008) *Adv. Drug Deliv. Rev.* 60:1252-1265; Klippstein and Pozo (2010) *Nanomedicine* 6:523-529). Owing to these unique physicochemical and functional properties, nanoparticles have been used as carriers for Ag delivery, with successful examples including enhancing the efficacy of dendritic cell-based cancer immunotherapy (Cho et al. (2011) *Nat. Nanotechnol.* 6:675-682; Hamdy et al. (2011) *Pharm. Res.* 28:2288-2301; Hirosue et al. (2010) *Vaccine* 28:7897-7906; Jewell et al. (2011) *Proc. Natl. Acad. Sci. USA* 108:15745-15750; Nembrini et al. (2011) *Proc. Natl. Acad. Sci. USA* 108:E989-997). Colloidal semiconductor nanocrystals, often referred to as QD, are a new generation of fluorescent dyes with advantage of brightness, photobleaching resistance, good chemical stability, and tunable spectral properties compared with traditional organic fluorophores and fluorescent-tagging molecules (Mattoussi et al. (2000) *J. Am. Chem. Soc.* 122:12142-12150; Boyle et al. (2011) *Biophys. J.* 101:L57-L59). Ab-conjugated QD were developed for high-resolution labeling and used to show the coclustering of TCR and CD4 or CD8 coreceptor in microclusters in recently activated T cells (Zhong et al. (2009) *PLoS ONE* 4:e5945; Pathak et al. (2007) *Nano Lett.* 7:1839-1845). In this study, the unique properties of Ab-coated QD were exploited, not for imaging, but rather to selectively activate Ag-specific T cells.

Although soluble anti-CD3 acts as a potent T cell mitogen, activating T cells indiscriminate of TCR specificity (Van Wauwe et al. (1980) *J. Immunol.* 124:2708-2713), it was found that anti-CD3 constrained on the surface of a nanoparticle specifically activated Ag-experienced T cells. Thus, by constraining anti-CD3 on the surface of nanoparticles, selectivity was imparted. Without being bound by any particular theory, it is hypothesized that this selectivity was due to the fact that, unlike naïve T cells, Ag-activated T cells display microclusters of the TCR on their surface (Fahmy et al. (2001) *Immunity* 14:135-143; Zhong et al. (2009) *PLoS ONE* 4:e5945; Boyle et al. (2011) *Biophys. J.* 101:L57-L59)). TCRs in these clusters were more sensitive to cross linking by the anti-CD3-coated nanoparticles than were TCR dispersed in smaller clusters across the surface of naïve cells. In support of this hypothesis is the finding that T cells that have been rested for 6 d after Ag stimulation, and still displayed TCR microclusters, remained sensitive to activation by anti-CD3-coated nanoparticles. In addition, preliminary studies employing (larger) 100-nm CD3-gold particles have activated both naïve and Ag-experienced T cells. Future studies employing a series of anti-CD3-coated gold particles of varying sizes will better define the relationship between the cluster size and the selective responsiveness to anti-CD3-constrained agonists. Alternatively, it is possible that the ability of anti-CD3-coated nanoparticles to selectively activate Ag-specific T cells was not due to the differences in microclusters exhibited by activated and resting T cells. It may be that the signaling machinery of previously activated T cells is more sensitive to limited exposure of anti-CD3 than resting T cells. Indeed, the kinetic segregation model suggests that these differences in response to Ag were due to the local changes in the balance of kinases and phosphatases associated with the TCR (Davis et al. (2006) *Nat. Immunol.* 7:803-809). Thus, it is possible that the results were not secondary to clustering per se, but rather due to changes in the topography of kinases and phosphatases in the Ag-experienced cells that make them more sensitive to activation when anti-CD3-coated nanoparticles engage TCR.

The in vivo data suggest that anti-CD3-coated nanoparticles could be employed clinically to enhance the magnitude of the response to vaccines for both infectious diseases as well as tumors. In vivo, the administration of the anti-CD3-coated nanoparticles enhanced the frequency of the Ag-specific T cells without any evidence of nonspecific T cell activation. Such findings suggest that the coadministration of Ag and anti-CD3-coated nanoparticles lead to the enhancement of the T cell responses. Furthermore, it was found that the administration of anti-CD3-coated nanoparticles during the initial encounter with Ag can result in increased generation of memory cells. Indeed, the mice treated with the anti-CD3-coated nanoparticles demonstrated increased recall responses upon rechallenge 10 d later. Such a finding suggests that this strategy might be employed to enhance the efficacy of preventative vaccines by boosting the generation of memory cells.

The presently disclosed findings have broad implications for promoting specificity even outside of the immune system. The selectivity of receptor-ligand interactions imparts signaling specificity. The specific expression of receptors on different cell types enables biologic selectivity. However, broad distribution of a receptor can present a hurdle to developing pharmacologic agents. The benefits of the specific biochemical pathways blocked or induced by ligand specificity may be mitigated by the fact that receptor is expressed on a diversity of cells. One such example of this is seen in the use of the anti-lymphoma agent anti-CD20 (rituximab) (Maloney et al. (1997) *Blood* 90:2188-2195). CD20 is expressed on lymphoma cells (Anderson et al. (1984) *Blood* 63:1424-1433), and indeed, rituximab is efficient at destroying tumor cells. In contrast, the expression of CD20 on all B cells means that a consequence of treatment is the depletion of nonmalignant B cells. If CD20 is clustered on lymphoma cells when compared with normal B cells, it is possible that constraining anti-CD20 on the surface of a nanoparticle might demonstrate greater selectivity for lymphoma cells. That is, constraining a particular ligand on the surface of a nanoparticle may promote the targeted activation of its receptor selectively on the desired cell type.

Example 2

Programmed cell death protein 1 (PD-1) is a critical immune-checkpoint receptor expressed on activated T cells to mediate immune suppression thus to prevent exaggerated and unwanted T cell activation (Pardoll (2012) *Nat. Rev. Cancer* 12:252-264). Using anti-PD-1 blocking antibody has been widely studied to enhance immunity to tumors or infectious diseases (Porichis and Kaufmann (2012) *Curr. HIV/AIDS Rep.* 9:81-90; Topalian et al. (2012) *N. Engl. J. Med.* 366:2443-2454). Given that PD-1 was reported to accumulate at the immunological synapse upon the T cell-APC conjugation (Pentchava-Hoang et al. (2007) *Proc. Natl. Acad. Sci. USA* 104:17765-17770) and form microclusters during T cell activation (Parry et al. (2005) *Mol. Cell Biol.* 25:9543-9553; Yokosuka et al. (2012) *J. Exp. Med.* 209:1201-1217; Matsumoto et al. (2004) *J. Immunol.* 172:2530-2541), it was determined whether the difference in the distribution pattern of surface PD-1 between naïve and activated T cells could be exploited to selectively signal only the T cells that had previously engaged antigen.

As in Example 1, confocal microscopy was employed to image the distribution of PD-1 on T cells before and after antigen exposure. Naïve T cells showed few clusters and a relatively low expression of PD-1 on the surface (FIG. 14A). After 24 hours of stimulation in vitro with cognate protein, the formation of PD-1 microclusters were observed over the surface of the activated T cells (FIG. 14B). Even after 6 days of rest, stimulated T cells still demonstrate a high degree of PD-1 clustering on the surface (FIG. 14C). It was postulated that the different degrees of PD-1 clustering on the surface of antigen-experienced versus naïve T cells could be exploited to selectively inhibit only the T cells that were recently activated (FIG. 15).

As shown in Example 1, constraining anti-CD3 antibodies on the surface of appropriate-sized nanoparticles allowed them to preferentially activate antigen-experienced T cells (as opposed to soluble antibodies) enhancing antigen-specific activation. In the present example, it was tested whether constraining anti-PD-1 antibodies on the surface of nano-size gold particles could change their effect on T cell activation as compared to soluble anti-PD-1 antibodies.

To test this hypothesis, naïve OT-1 splenocytes were incubated in vitro with class I OVA peptide together with medium, soluble anti-PD-1 (clone G4, G4) or gold-constrained-anti-PD-1 (Gold-G4) and evaluated for proliferation. G4 is a clone of anti-PD-1 antibody that was previously shown to block the B7-H1/PD-1 negative signaling pathway (Matsumoto et al. (2004) *J. Immunol.* 172:2530-2541). $CD8^+$ T cells incubated with peptide proliferated modestly, while the addition of soluble G4 resulted in enhancement of proliferation (FIG. 16). Interestingly, the proliferation of $CD8^+$ T cells incubated with peptide was markedly suppressed when Gold-G4 were present in the culture (FIG. 16). This in vitro experiment shows that: (1) G4 enhances T cell activation; and (2) by constraining G4 antibodies on the surface of nanoparticles, it selectively inhibits antigen-specific CD8+ T cell activation.

Next, it was determined whether T cells activated in vivo rendered them susceptible to be selectively inhibited by Gold-G4. Treatment with G4 led to an enhancement in the frequency of vaccine-induced antigen-specific CD8+ Thy1.1+OT-1 T cells in the peripheral blood compared to that detected from animals given PBS (FIG. 17). However, treatment with Gold-G4 led to a decrease in the frequency of vaccine-induced antigen-specific CD8+ Thy1.1+OT-1 T cells compared to that detected from animals given PBS (FIG. 17). This indicates that Gold-G4 is able to selectively inhibit antigen-specific T cells response in vivo.

Overall these studies demonstrate that constraining anti-PD-1 antibody (G4 clone) on the surface of a nanoparticle can promote the selective inhibition of antigen activated T cells. Thus, this reagent would be useful for the treatment of autoimmune diseases and the prevention of rejection in transplantation.

There is another anti-PD-1 antibody, clone RMP1-30, which is used for staining of cells and has no reported ability to block B7-H1/PD-1 negative signaling (Matsumoto et al. (2004) *J. Immunol.* 172:2530-41). Naïve OT-1 splenocytes were stimulated in vitro with class I OVA peptide together with medium, soluble anti-PD-1 (RMP1-30), or Gold-anti-PD-1 (Gold-RMP) and evaluated for proliferation. CD8+ T cells incubated with peptide proliferated modestly, while the addition of RMP1-30 resulted in marked suppression of proliferation (FIG. 18A). Strikingly, the proliferation of CD8+ T cells incubated with peptide was markedly enhanced when Gold-RMP was present in the culture (FIG. 18A). Furthermore, these proliferating cells produced robust IFN-γ (FIG. 18B). OT-1 cells cultured with Gold-RMP also had a much higher level of IFN-γ secretion compared to cells cultured with medium alone or soluble RMP1-30 (FIG. 18C). This in vitro experiment demonstrated that: (1) RMP anti-PD-1 antibody suppressed T cell activation; and (2) constraining RMP on the surface of a nanoparticle lead to the selective enhancement of antigen specific T cells.

Again, PCC-specific 5C.C7 T cells were utilized to test the effect of Gold-RMP on CD4+ T cells. The addition of soluble anti-PD-1 (RMP1-30) markedly suppressed the proliferation of CD4+ T cells incubated with PCC peptide (FIG. 19A). In contrast, the proliferation of CD4+ T cells incubated with peptide was enhanced when Gold-RMP were present in the culture (FIG. 19B).

Finally, it was determined whether gold-anti-PD-1 (RMP1-30) could enhance the immune response against tumor growth in vivo. MC38 mouse colon cancer cells were injected subcutaneously into mice. After 7 days, the tumors were measured and mice were treated with nothing or gold-anti-PD-1 (RMP1-30) every 3 days. Tumor burden of mice receiving gold-anti-PD-1 (RMP1-30) showed a markedly slower growth rate (FIG. 20). This suggested that constraining anti-PD-1 antibodies (RMP1-30) onto the surface of nano-sized gold particles were able to enhance endogenous immune response to control tumor growth.

Overall these studies identified RMP1-30-anti-PD-1 coated nanoparticles as a means to selectively enhance antigen specific T cell responses. These findings showed that RMP-coated nanoparticles can selectively enhance responses to preventative vaccines, treatment vaccines, and immunotherapy for treating and preventing both infectious diseases and cancer.

In addition, a means of delivering checkpoint blockade, which will be able to selectively enhance the activation of tumor-specific T cells without non-specifically activating potentially harmful T cell responses has been developed. The presently disclosed subject matter has important implications for the further development of PD-1 blockade clinically by enhancing anti-tumor immunity while mitigating the development of autoimmunity. Furthermore, the presently disclosed subject matter will potentially inform the strategic delivery of other checkpoint blockade antibodies such anti-CTLA-4 and anti-LAG-3.

Example 3

This Example further develops the finding that constraining activating antibodies, to the surface of nanoparticles targets these antibodies to cells that recently engaged specific antigen. Here the presently disclosed subject matter is applied to further experiments disclosing the delivery of anti-PD-1 to selectively enhance anti-tumor immunity without promoting autoimmunity.

Approach

The approach is built on the observation that clustering of PD-1 on the surface of T cells changes after activation. It is hypothesized that the differential spatial distribution of PD-1 on the surface of recently activated versus naïve or memory T cells could be exploited to selectively target T cells in an antigen-specific fashion (FIG. 21). In this Example, this approach is used to enhance the potency and selectivity of anti-PD-1 checkpoint blockade.

Figure 22:
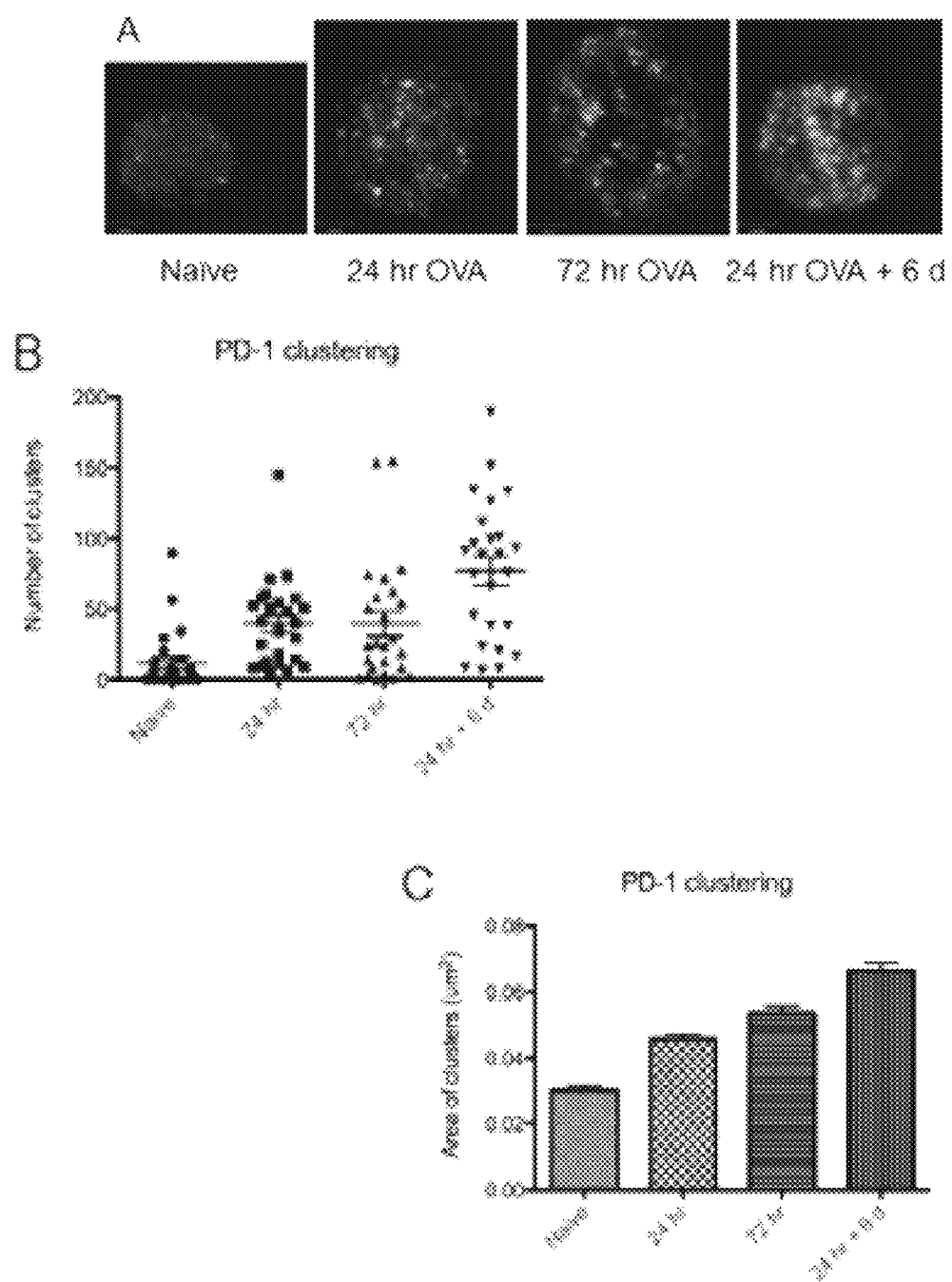

Antigen Activation Leads to the Sustained Formation of PD-1 Microclusters on the Surface of T Cells Confocal microscopy was employed to image the distribution of PD-1 on T cells before and after antigen exposure. Images were acquired 1 μm below the top of the cell, trading off sharpness for the largest area of membrane in a single image. Naïve RAG2$^{-/-}$ CD8+OT-1 TCR transgenic T cells specific for OVAlbumin (OVA) were stained for the PD-1 signaling complex using purified anti-PD-1 and Alexa 488 labeled secondary antibody and imaged. Naïve T cells showed few clusters and a relatively uniform distribution of PD-1 on the surface (FIG. 22). After 24 to 72 hours of stimulation in vitro with 5 μg/mL class I OVA peptide, the formation of PD-1 microclusters over the surface of the activated T cells was observed (FIG. 22). Furthermore, when the cells were stimulated for 24 hours with antigen and then rested in the absence of antigen for 6 days, the PD-1 microclusters were not only still prevalent but actually significantly increased. Thus, PD-1 microclusters on the cell surface could distinguish T cells that had seen antigen versus those that had not.

Anti-PD-1 Constrained to a Nanoparticle Enhances T Cell Activation

In light of the observation that PD-1 (like CD3) forms microclusters upon activation, the ability of anti-PD-1 constrained to a nanoparticle to enhance T cell activation was tested. A number of anti-PD-1 antibodies was screened and it was observed that while soluble RMP1-30 anti-PD-1 antibody (eBioscience, Cat No. 13-9981-85) did not enhance T cell responses, this antibody when constrained to the surface of a nanoparticle potently enhanced T cell activation (FIGS. 18B and 18C). Furthermore, this activation was selective in that there was not increased activation in the absence of peptide (data not shown) and while anti-PD-1 coated nanoparticles enhanced antigen specific T cell responses to Ova, they did not cause non-specific activation of the non-Ova-specific T cells (FIG. 23).

RMP1-30 anti-PD1 constrained to a nanoparticle was next tested to see if it could enhance T cell activation in vivo. Thy1.2+ C57B1/6 mice were injected s.c. with 0.5×10$^6$ B16 OVA tumor cells. At day 7, tumor size was measured by caliber and mice were rearranged into two groups bearing equal average size of tumors. 10$^6$ OT-1 Thy1.1+ cells and 10$^6$ PFU of Vaccinia-OVA were injected i.v. with or without anti-PD-1 Gold i.v. At day 13, the addition of anti-PD-1 gold nanoparticles led to a marked increase in the OVA specific T cells (FIG. 24). That is, in this experiment, anti-PD-1 coated gold nanoparticles enhanced the efficacy of the vaccine even in the presence of growing OVA expressing tumor.

Anti-PD-1 Coated Nanoparticles Lead to the Segregation of PD-1 and TCR on the Surface of the T Cell.

It was next determined what the effect of treatment with anti-PD-1 coated nanoparticles was on PD-1 clustering. As seen in FIG. 25, treatment of antigen activation of OT-1 T cells in the presence of the anti-PD-1 coated nanoparticles leads to the segregation of TCR and PD-1 microclusters. This segregation is not observed when the soluble anti-PD-1 is added. The presence of anti-PD-1 coated nanoparticles led to an increase in antigen-induced PKC theta and mTOR signaling (data not shown). These preliminary studies suggest that anti-PD-1 coated nanoparticles can enhance T cell activation by promoting the segregation of TCR and PD-1 leading to enhanced downstream signaling.

Anti-PD-1 Constrained to the Surface of a Nanoparticle Will Selectively Enhance Tumor-Specific T Cell Responses.

Properties and Preparation of Anti-PD-1 Coated Gold Nanoparticles and Quantum Dots (QD):

The gold nanoparticles are 40 nm in diameter and are coated with approximately 9 molecules of streptavidin. Biotin is conjugated to anti-PD-1 using the EZ-Link® NHS-PEO4-Biotinylation Kit. Based on the constraints imposed by the antibody molecules, there are approximately 7-9 (Fc bound) anti-PD-1 antibodies per nanoparticle. For in vitro experiments, a final concentration of $2.3 \times 10^9$ particles/mL is used. For subcutaneous delivery, a minimal starting dose of $6.0 \times 10^{11}$ particles per injection is employed. This dose was loosely calculated on the number of particle injected for in vivo whole body imaging. In addition, this is the dose that was effective in in vivo studies employing anti-CD3 coated quantum dots. For I.V. delivery, the minimal starting dose is $3.57 \times 10^{16}$ particles per injection (this was the dose employed in FIG. 24). Imaging studies have demonstrated the distribution of I.V. injected nanoparticles in the blood, to the spleen, liver and lymph nodes, and this will be investigated. For imaging studies, protein A quantum dots using commercial QD from Ocean Nanotech will be prepared.

Optimizing the Potency and Specificity of Anti-PD-1 Coated Nanoparticles:

Initial experiments will employ the MC38 colon cancer model. MC38-OVA tumor cells ($10^6$ cells) will be injected subcutaneously into syngeneic C57B16 mice. After 12 days of tumor growth, the mice will be treated on day 12, 16 and 20 with vehicle (negative treatment control), 100 µg of soluble anti-PD-1 which has previously been shown to delay tumor growth in this model (positive control for the effect of soluble anti-PD-1 blocking antibody in this model) or RMP1-30 coated gold nanoparticles injected subcutaneously. The initial dose will be approximately $6.0 \times 10^{11}$ particles per injection which is the dose that was previously established as being able to enhance the immune response to antigen+adjuvant for anti-CD3 coated nanoparticles. Based on efficacy (see below), the dose may be needed to be increased, which will be determined empirically by increasing by factors of 10 the number of particles (e.g., one group injected $9.6 \times 10^{12}$ particles per injection S.C.). In addition, the schedule may be altered if necessary. The initial schedule is based on that employed for soluble anti-PD-1. However, it may be that the anti-PD-1 constrained to a nanoparticle might need to be given more frequently. To this end, the distribution of the nanoparticles will be monitored in the blood and tumor draining lymph nodes and the schedule will be altered empirically as well as to maximize distribution. Studies indicate that gold nanoparticles have a robust safety profile in mice. Nonetheless, potential toxicity will be determined by measuring weight loss, fur ruffling, and lethargy. In addition, BUN/Cr will be monitored as well as liver enzymes and synthetic function.

Efficacy will be determined by monitoring the mice for tumor growth. In addition, cohorts of mice will be sacrificed at day 30 and their spleens will be monitored for tumor specific (OVA as an engineered tumor antigen) responses. To this end, spleen and draining lymph nodes will be assessed for the proliferation and activation of OVA specific $CD8^+$ T cells using the OVA specific MHC class I tetramer (Beckman Coulter #T03000). Specifically, the activation status (CD44, CD69, CD621, KLRG (effector) and CD127 (memory)) of the tetramer positive versus the tetramer negative cells will be examined. In addition, splenocytes and lymph node cells will be activated with OVA peptide and IFN-γ, TNF and IL-2 production will be assessed by both intracellular staining and ELISA.

Demonstrating the Ability of Anti-PD-1 Coated Nanoparticles to Selectively Enhance Anti-Tumor Responses.

It is hypothesized that anti-PD-1 coated nanoparticles given after the growth of tumor will selectively enhance the tumor specific T cells and NOT induce the activation of T cells with specificity for influenza antigen. To this end, the mice will first be vaccinated with an intranasal dose of 300 EID50 of the A/X-31(H3N2) attenuated influenza virus in a total volume of 30 µL (15 µL per nostril). This virus has been shown previously to generate a robust CD8 T cell mediated immune response when used in this manner, and to result in a stable memory T cell population. This will lead to the generation of influenza specific T cells that can be tracked using tetramers. At 21 days, identification of a population of influenza-specific (tetramer+) T cells that no longer have clustered PD-1 on their surface (as determined by microscopy) is expected. At this point, the mice will be challenged with MC38-OVA tumor cells ($10^6$ cells) and subsequently treated with anti-PD-1 coated nanoparticles beginning on day 12 post tumor challenge. Survival and immunologic studies will be performed as described above. However, additionally the lymphocytes will be stained with a nucleoprotein peptide, NP366-374 (ASNENMETH), loaded MHC class I tetramer and the frequency and activation status of these cells will be determined in the mice receiving no treatment, treatment with soluble anti-PD-1 and treatment with anti-PD-1 coated nanoparticles. It is predicted that the anti-PD-1 coated nanoparticles will enhance the response to MC38-OVA cells, but will not lead to the activation of Flu-specific memory T cells.

Demonstrate that Anti-PD-1 Coated Nanoparticles Enhance the Efficacy of a Tumor Vaccine:

Experiments will be performed to demonstrate the ability of anti-PD-1 coated nanoparticles to enhance the efficacy of a tumor vaccine using the B16 melanoma model. In this model, a GMCSF secreting whole cell vaccine can delay tumor growth but does not lead to the eradication of the tumor. Syngeneic C57B16 (Thy1.1+) mice will be injected with $2 \times 10^5$ B16 melanoma cells. In addition, at this time the mice will be infused i.v. with $1 \times 10^7$ fresh TCR-transgenic (Thy1.2+) pmel-1 T cells. Beginning 7 days post tumor challenge, the mice will receive GVAX ($1.5 \times 10^6$ irradiated B16 tumor cells and $1.5 \times 10^6$ irradiated bystander GM-CSF secreting 3T3 cells). In addition, the mice will be treated with either vehicle alone or the optimal dose of anti-PD-1 coated nanoparticles beginning on Day 7. On day 28 post-tumor challenge, the mice will be sacrificed and examined for tumor burden in the lungs and immunologic response. That is, spleen and draining lymph nodes will be assessed for the proliferation and activation of pmel-1 CD8+ T cells. Specifically, the activation status (CD44, CD69, CD62L, KLRG1 and CD127) of the Thy1.2 positive versus the Thy1.2 negative cells will be examined. In addition, splenocytes and lymph node cells will be activated after 4 h of stimulation with 1 µM mgp100 peptide and tested for cytokine production.

Predicted and Potential Alternative Outcomes:

The premise of this Example is that constraining anti-PD-1 on the surface of a nanoparticle will selectively lead to robust enhancement of anti-tumor responses without non-specific activation of naïve or memory T cells. It is predicted that the anti-PD-1 coated nanoparticles will promote the immunologic rejection of the MC38 tumor cells. Preliminary in vitro data suggest that RMP1-30 coated nanoparticles are more potent than soluble anti-PD-1. An important aspect will be to optimize the delivery of the nanoparticles. First, preliminary experiments employed nanoparticles 40 nm in size. It may be that by increasing the size of the nanoparticles, anti-tumor immune responses will be enhanced. Of note, this was the case for anti-CD3 coated nanoparticles, but as 100 nm was approached, some of the selectivity was lost.

Overall determining the optimal dosing and schedule will be somewhat empirical. The initial dose was based on the distribution of nanoparticles in vivo in imaging studies. The initial schedule was based on the schedule for soluble anti-PD-1 in this model. An advantage of working with nanoparticles is that in addition to efficacy (tumor size) and immunologic (measuring the activation of antigen specific T cells) parameters, draining lymph nodes and tumor can be imaged for presence of nanoparticles as a means of maximizing dose and schedule. With regard to the route of delivery, the previous data support the role for subcutaneous delivery. However, as seen in FIG. 24, I.V. delivery also worked for the B16 melanoma model. Previous studies have shown that nanoparticles in the 40 nm size range, injected I.V. demonstrate prolonged blood circulation time so it is believed that this route is worthy of continued consideration.

A limitation of in this Example is that OVA is not truly a tumor antigen. However, the reagents available will greatly facilitate the ability to optimize anti-PD-1-nanoparticle delivery. Furthermore, in some respects, OVA does mimic a highly expressed mutated immunogenic antigen that one might see in colon cancer with microsatellite instability. Once the delivery is optimized, the response of T cells to endogenous tumor antigen will be examined. Also, vaccine experiments in genetically engineered tumor models using K-ras mice breeding can be initiated.

It is predicted that the anti-PD-1 coated nanoparticles will enhance the efficacy of the anti-tumor vaccine. This will be tested functionally by measuring tumor burden in the lungs as well as assessed immunologically by interrogating the anti-tumor response. Further, it is predicted that the anti-PD-1 coated nanoparticles will enhance the anti-tumor response but not induce non-specific activation of irrelevant T cells. Specifically, it is predicted that the anti-PD-1 coated nanoparticles will not induce activation of the resting anti-Flu specific T cells. It is possible that at 21 days there will still be PD-1 clustering and hence activation of the influenza-specific T cells. If such is the case, then a kinetics experiment will be performed to determine precisely how long the PD-1 clustering lasts in vivo after the influenza vaccination.

Anti-PD-1 Nanoparticles Enhance T Cell Responses by Segregating PD-1 and TCR.

Initial experiments employing a number of anti-PD-1 antibodies revealed that RMP1-30 was the most potent enhancer of T cell activation when constrained on the surface of a nanoparticle (FIG. 23, and data not shown). On the other hand, soluble RMP1-30 did not enhance T cell responses. The functional differences between soluble RMP1-30, which does not enhance T cell responses, and RMP1-30 constrained on the surface of a nanoparticle, which does enhance T cell responses, affords the opportunity to investigate the mechanism of enhancement. Indeed, preliminary data suggests that mechanistically, this is due to the segregation of PD-1 and TCR microclusters (FIG. 25).

Enhancement of T Cell Activation by Anti-PD-1 Coated Nanoparticles is the Result of Segregating PD-1 and TCR Microclusters:

Naïve RAG2$^{-/-}$ CD8$^+$OT-1 TCR transgenic T cells specific for OVAlbumin (OVA) will be stimulated in vitro with 5 µg/mL class I OVA peptide in the presence of naked nanoparticles (negative control), soluble RMP1-30, and RMP1-30 coated nanoparticles for 24, 48 and 72 hours. For each time point, PD-1 and TCR clustering will be evaluated by: a) labeling with them with QD of different colors, emitting at 605 nm or 655 nm (but excited at the same wavelength), conjugated to anti-PD-1 or anti-CD3 (see above for more details of the conjugation to either gold or QD), b) imaging the labels for colocalization using the approach of Costes et al. embodied in the ImageJ plugin JCOP. The extent of clustering of PD-1 and CD3 will be analyzed using kICS analysis, which yields measures of extent of label clustering and size of clusters, as well as lateral diffusion of the labeled molecules. Since polyvalent labels may perturb the native distribution of PD-1 and CD3, monOVAlent QD will be used, either prepared by titrating proteinA QD (see above) or by synthesizing explicitly monOVAlent QD by using aptamers to block binding of more than one protein A or antibody to the QD surface.

Anti-PD-1 Coated Nanoparticles Promotes Anti-TCR Induced Signaling:

The precise details by which PD-1 inhibits T cell function remain incomplete. A number of studies have demonstrated the ability of PD-1 to inhibit proximal TCR signaling by recruiting the phosphatase SHP2 to the immunologic synapse. This leads to inhibition of TCR-induced ZAP70 activation. Likewise, distally, it has been shown that PD-1 inhibits mTOR activation in part through the regulation of PTEN. The hypothesis that RMP1-30 anti-PD-1 coated nanoparticles promote increased T cell activation by abrogating these inhibitory mechanisms will be tested.

Splenocytes from OT-1 Rag2$^{-/-}$ mouse will be stimulated in the presence of 5 µg/mL class I OVA peptide for 24 hours and then rested in 100 ng/mL IL-2 and 10 ng/mL IL-7 for 5 days to create previously activated T cells. Live lymphocytes will be isolated and stimulated anti-CD3 (1 µg/mL), anti-CD28 (2 µg/mL) and antibody to hamster IgG1 (0.75 µg/mL; G94-56; BD Biosciences) in combination with nothing, soluble RMP1-30 or gold constrained RMP1-30 for 3 hours. The cells will be lysed and lysates will be interrogated by western blot for phosphorylation of ZAP70 (proximal signaling), phosphorylation of IKB (NF-kB pathway), phosphorylation of Erk (AP-1 pathway) and NF-AT translocation to the nucleus. In addition, PD-1 and CD3 will be immunoprecipitated and then blotted for the presence of SHP2. Finally, cell lysates will be interrogated for phosphorylation of Akt at Threonine 308 (which is upstream of mTOR signaling), phosphorylation of Akt at Serine 473 (which is downstream of mTORC2 signaling) and phosphorylation of S6K1 (which is downstream of mTORC1 signaling).

Predicted Outcomes:

Based on the preliminary data, it is predicted that the dichotomous outcomes of soluble RMP1-30 versus nanoparticle constrained RMP1-30 are due to differences in the ability of these two reagents to promote the segregation of PD-1 and TCR microclusters. While there are powerful tools for measuring and analyzing the distribution of TCR and PD-1, the results may not show spatial segregation resolvable on the light microscope scale. If kICS analysis of clustering suggests that there is segregation on the nm scale, then antibody-gold nanoparticles can be used for immune-EM of the distribution.

It is predicted that RMP1-30 coated nanoparticles will lead to decreased SHP2 recruitment, increased ZAP70 and downstream signaling. However, it may be that anti-PD-1 coated nanoparticles have a minimal effect on enhancing downstream TCR signaling but rather influence PTEN expression and recruitment. If such is the case, then the findings might provide important clues as to the mechanisms by which PD-1 inhibits downstream mTOR signaling. Either outcome should provide important insight into the mechanism of PD-1 mediated inhibition.

It is believed that the data will have important implications for the potential future rational design of more clinically potent anti-PD-1 antibodies. For example, it may be that a means for screening the potential efficacy of anti-PD-1 (or even anti-CTLA-4 or anti-LAG3) antibodies will be to determine the ability of such antibodies to promote segregation from these checkpoint inhibitors and the TCR. To this end, it is presently unclear why RMP1-30 proved to be the most potent antibody of the ones screened. However, in the future, the epitopes of antibodies that promote the segregation of PD-1 and TCR versus those that do not might be mapped.

Furthermore, the presently disclosed subject matter provides important insight into the mechanism by which anti-PD-1 constrained to a nanoparticle can robustly enhance T cell responses. These data enables insight into the mechanism by which PD-1 inhibits T cells. In addition, the approach of constraining antibodies on the surface of a nanoparticle to impart cellular specificity is generalizable to target other ligand receptor interactions. For example, anti-CD20 therapy (Rituxan) is an integral part of treatments for Lymphoma. However, anti-CD20 therapy indiscriminately depletes the body of normal B cells as well as lymphoma. If the spatial organization of CD20 is different on the surface of lymphomas when compared to normal B cells, then anti-CD20 coated nanoparticles can be engineered to selectively target lymphoma.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for selectively enhancing activation of antigen-experienced T cells, the method comprising:
   a) administering a selected antigen to T cells in an amount sufficient to produce microclustering of ligand-binding receptors on the surface of the T cells, thereby producing antigen-experienced T cells comprising microclustered ligand-binding receptors; and
   b) administering nanocarrier-associated ligands and the selected antigen to the antigen-experienced T cells, wherein the ligand-binding receptors bind ligands selected from the group consisting of anti-CD3 antibodies, anti-PD-1 antibodies, and functional variants thereof;
   wherein the nanocarrier-associated ligands bind the microclustered ligand-binding receptors of the antigen-experienced T cells, thereby selectively enhancing activation of the antigen-experienced T cells as compared to:
      i) the binding of free ligands to the microclustered ligand-binding receptors of the antigen-experienced T cells; and
      ii) the binding of nanocarrier-associated ligands to ligand-binding receptors of nave T cells, wherein the nave T cells are non-specifically activated.

2. The method of claim 1, wherein the T cells are selected from the group consisting of CD4$^+$ T cells or CD8$^+$ T cells.

3. The method of claim 1, wherein selectively enhancing activation of the antigen-experienced T cells as compared to the naïve T cells comprises selectively enhancing an antigen-specific T cell response in the antigen-experienced T cells as compared to the naïve T cells.

4. The method of claim 3, wherein the antigen-specific T cell response comprises enhanced proliferation of the antigen-experienced T cells as compared to the naïve T cells.

5. The method of claim 3, wherein the antigen-specific T cell response comprises promoting the generation and function of specific effector cells from the antigen-experienced T cells as compared to the naïve T cells.

6. The method of claim 5, wherein promoting the generation and function of specific effector cells from the antigen-experienced T cells comprises increasing the number of antigen-experienced T cells producing one or more proteins.

7. The method of claim 6, wherein the one or more proteins comprise interleukins.

8. The method of claim 7, wherein the interleukins comprise IL-12 or IL-4.

9. The method of claim 3, wherein the enhanced response of the antigen-experienced T cells as compared to the naïve T cells comprises vaccine-induced proliferation of antigen-experienced T cells and generation of functional memory cells.

10. The method of claim 1, wherein the antigen is a protein or peptide.

11. The method of claim 1, wherein the ligand-binding receptors are T cell receptors.

12. The method of claim 1, wherein the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials.

13. The method of claim 1, wherein the nanocarrier-associated ligands are associated with nanocarriers with a mean geometric diameter that is less than 100 nm.

14. A method for treating infectious disease or cancer in a subject in need thereof, the method comprising administering to the subject:
   a) a selected antigen in an amount sufficient to produce microclustering of ligand-binding receptors on the surface of T cells in the subject, thereby producing antigen-experienced T cells comprising microclustered ligand-binding receptors; and
   b) nanocarrier-associated ligands in an amount sufficient for the nanocarrier-associated ligands to bind microclustered ligand-binding receptors of the antigen-experienced T cells, wherein the ligand-binding receptors bind ligands selected from the group consisting of anti-CD3 antibodies, anti-PD-1 antibodies, and functional variants thereof, thereby selectively enhancing activation of the antigen-experienced T cells as compared to:
      i) the binding of free ligands to the microclustered ligand-binding receptors; and
      ii) the binding of nanocarrier-associated ligands to ligand-binding receptors of naïve T cells, wherein the naïve T cells are non-specifically activated.

15. The method of claim 14, wherein the selected antigen and the nanocarrier-associated ligands are administered to the subject concurrently.

16. The method of claim 14, wherein the selected antigen and the nanocarrier-associated ligands are administered to the subject sequentially.

17. The method of claim 14, wherein the T cells are selected from the group consisting of CD4$^+$ T cells or CD8$^+$ T cells.

18. The method of claim 14, wherein selectively enhancing activation of the antigen-experienced T cells as compared to the naïve T cells comprises selectively enhancing an antigen-specific T cell response in the antigen-experienced T cells as compared to the naïve T cells.

19. The method of claim 18, wherein the antigen-specific T cell response comprises enhanced proliferation of the antigen-experienced T cells as compared to the naïve T cells.

20. The method of claim 18, wherein the antigen-specific T cell response comprises promoting the generation and function of specific effector cells from the antigen-experienced T cells as compared to the naïve T cells.

21. The method of claim 20, wherein promoting the generation and function of specific effector cells from the antigen-experienced T cells comprises increasing the number of antigen-experienced T cells producing one or more proteins.

22. The method of claim 21, wherein the one or more proteins comprise interleukins.

23. The method of claim 22, wherein the interleukins comprise IL-12 or IL-4.

24. The method of claim 18, wherein the enhanced response of the antigen-experienced T cells to a vaccine as compared to the naïve T cells comprises vaccine-induced proliferation of antigen-experienced T cells and generation of functional memory cells.

25. The method of claim 14, wherein the antigen is a protein or peptide.

26. The method of claim 14, wherein the ligand-binding receptors are T cell receptors.

27. The method of claim 14, wherein the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials.

28. The method of claim 14, wherein the nanocarrier-associated ligands are associated with nanocarriers with a mean geometric diameter that is less than 100 nm.

29. A method for selectively enhancing activation of cancer cells comprising microclustered ligand-binding receptors, the method comprising administering nanocarrier-associated ligands to a plurality of cells, wherein the plurality of cells comprises:
   a) cancer cells comprising microclustered ligand-binding receptors; and
   b) cells comprising non-microclustered ligand-binding receptors;
   wherein the nanocarrier-associated ligands selectively bind microclustered ligand-binding receptors, thereby selectively enhancing activation of cancer cells comprising microclustered ligand-binding receptors as compared to cells comprising non-microclustered ligand-binding receptors, and wherein the ligand-binding receptors bind ligands selected from the group consisting of anti-CD3 antibodies, anti-PD-1 antibodies, and functional variants thereof.

30. The method of claim 29, wherein the nanocarrier-associated ligands are anti-cancer agents, and wherein selectively enhancing activation of cancer cells comprising microclustered ligand-binding receptors comprises destroying the cancer cells.

31. The method of claim 29, wherein the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials.

32. The method of claim 29, wherein the nanocarrier-associated ligands are associated with nanocarriers with a mean geometric diameter that is less than 100 nm.

33. A composition for selectively enhancing activation of antigen-experienced T cells, the composition comprising:
   a) a selected antigen in an amount sufficient to produce microclustering of ligand-binding receptors on the surface of T cells, thereby producing antigen-experienced T cells comprising microclustered ligand-binding receptors; and
   b) nanocarrier-associated ligands in an amount sufficient for the nanocarrier-associated ligands to bind microclustered ligand-binding receptors of the antigen-experienced T cells, wherein the ligand-binding receptors bind ligands selected from the group consisting of anti-CD3 antibodies, anti-PD-1 antibodies, and functional variants thereof, thereby selectively enhancing activation of the antigen-experienced T cells as compared to:
      i) the binding of free ligands to the microclustered ligand-binding receptors; and
      ii) the binding of nanocarrier-associated ligands to ligand-binding receptors of naïve T cells, wherein the naïve T cells are non-specifically activated.

34. The composition of claim 33, wherein the T cells are selected from the group consisting of CD4$^+$ T cells or CD8$^+$ T cells.

35. The composition of claim 33, wherein the antigen is a protein or peptide.

36. The composition of claim 33, wherein the ligand-binding receptors are T cell receptors.

37. The composition of claim 33, wherein the nanocarrier-associated ligands are associated with nanocarriers selected from the group consisting of lipid nanoparticles, polymeric nanoparticles, metallic nanoparticles, carbon nanoparticles, surfactant-based emulsions, dendrimers, and nanoparticles developed using a combination of nanomaterials.

38. The composition of claim 33, wherein the nanocarrier-associated ligands are associated with nanocarriers with a mean geometric diameter that is less than 100 nm.

* * * * *